US012618031B2

(12) United States Patent
Chua et al.

(10) Patent No.: US 12,618,031 B2
(45) Date of Patent: May 5, 2026

(54) DELIVERY DEVICES

(71) Applicant: THE METHODIST HOSPITAL SYSTEM, Houston, TX (US)

(72) Inventors: Ying Xuan Chua, Houston, TX (US); Alessandro Grattoni, Houston, TX (US); Jesus Paez Mayorga, Houston, TX (US); Simone Capuani, Houston, TX (US)

(73) Assignee: THE METHODIST HOSPITAL SYSTEM, Houston, TX (US)

( * ) Notice: Subject to any disclaimer, the term of this patent is extended or adjusted under 35 U.S.C. 154(b) by 717 days.

(21) Appl. No.: 18/003,231

(22) PCT Filed: Jun. 24, 2021

(86) PCT No.: PCT/US2021/038816
§ 371 (c)(1),
(2) Date: Dec. 23, 2022

(87) PCT Pub. No.: WO2021/262931
PCT Pub. Date: Dec. 30, 2021

(65) Prior Publication Data
US 2023/0265371 A1 Aug. 24, 2023

Related U.S. Application Data

(60) Provisional application No. 63/043,439, filed on Jun. 24, 2020.

(51) Int. Cl.
C12M 3/00 (2006.01)
A61F 2/02 (2006.01)
(Continued)

(52) U.S. Cl.
CPC ............. C12M 21/08 (2013.01); A61F 2/022 (2013.01); A61K 9/0024 (2013.01); A61K 35/39 (2013.01);
(Continued)

(58) Field of Classification Search
CPC ...... C12M 21/08; C12M 23/16; C12M 25/02; C12M 29/04; A61F 2/022; A61K 9/0024;
(Continued)

(56) References Cited

U.S. PATENT DOCUMENTS

| | | | | |
|---|---|---|---|---|
| 5,222,982 A | * | 6/1993 | Ommaya | ................ A61F 2/022 |
| | | | | 604/890.1 |
| 6,607,910 B1 | | 8/2003 | Dimitrijevich et al. | |

(Continued)

FOREIGN PATENT DOCUMENTS

| | | | | | |
|---|---|---|---|---|---|
| WO | WO-9403126 A1 | * | 2/1994 | ............. | A61F 2/022 |
| WO | WO-2010009307 A2 | * | 1/2010 | ............ | C12M 23/16 |

(Continued)

OTHER PUBLICATIONS

Extended European Search Report for European application No. 21829244.9 mailed Aug. 12, 2024.
(Continued)

*Primary Examiner* — Wesley G Harris
(74) *Attorney, Agent, or Firm* — Womble Bond Dickinson (US) LLP

(57) ABSTRACT

The present disclosure is directed to devices used for transplanting or recruiting cells, in addition to methods for making said devices and for using said devices in the treatment of medical disorders.

20 Claims, 20 Drawing Sheets

(51) Int. Cl.

| | |
|---|---|
| *A61K 9/00* | (2006.01) |
| *A61K 35/39* | (2015.01) |
| *A61K 35/545* | (2015.01) |
| *A61K 39/00* | (2006.01) |
| *A61L 27/38* | (2006.01) |
| *A61M 31/00* | (2006.01) |
| *A61M 37/00* | (2006.01) |
| *A61P 3/10* | (2006.01) |
| *A61P 35/00* | (2006.01) |
| *C12M 1/00* | (2006.01) |
| *C12M 1/12* | (2006.01) |
| *C12M 3/06* | (2006.01) |
| *C12N 5/078* | (2010.01) |

(52) U.S. Cl.
CPC ........ *A61K 35/545* (2013.01); *A61K 39/0011* (2013.01); *A61L 27/3804* (2013.01); *A61M 31/002* (2013.01); *A61M 37/00* (2013.01); *A61P 3/10* (2018.01); *A61P 35/00* (2018.01); *C12M 23/16* (2013.01); *C12M 25/02* (2013.01); *C12M 29/04* (2013.01); *C12N 5/0634* (2013.01); *C12N 2502/30* (2013.01)

(58) Field of Classification Search
CPC ... A61K 35/39; A61K 35/545; A61L 27/3804; A61M 31/002; A61M 37/00; A61P 3/10; A61P 35/00; C12N 5/0634; C12N 2502/30
See application file for complete search history.

(56) References Cited

U.S. PATENT DOCUMENTS

| | | | |
|---|---|---|---|
| 6,900,055 B1 | 5/2005 | Fuller et al. | |
| 7,361,195 B2 * | 4/2008 | Schwartz | A61L 27/3804 |
| | | | 623/23.63 |
| 2004/0171143 A1 | 9/2004 | Chin et al. | |
| 2013/0131628 A1 * | 5/2013 | Grattoni | A61P 3/00 |
| | | | 604/93.01 |
| 2017/0342363 A1 | 11/2017 | Fang et al. | |
| 2018/0085494 A1 | 3/2018 | Fawdry | |
| 2018/0235900 A1 * | 8/2018 | Swarner | A61K 9/0024 |
| 2019/0328934 A1 | 10/2019 | D'Amour | |
| 2021/0147779 A1 | 5/2021 | Cook et al. | |

FOREIGN PATENT DOCUMENTS

| | | | | |
|---|---|---|---|---|
| WO | WO-2017096297 A1 * | 6/2017 | | C12M 23/16 |
| WO | 2019079384 | 4/2019 | | |
| WO | 2020105381 | 5/2020 | | |
| WO | WO-2020105381 A1 * | 5/2020 | | A61K 35/39 |

OTHER PUBLICATIONS

International Search Report and Written Opinion for International Application No. PCT/US2021/038816, Oct. 14, 2021.

* cited by examiner

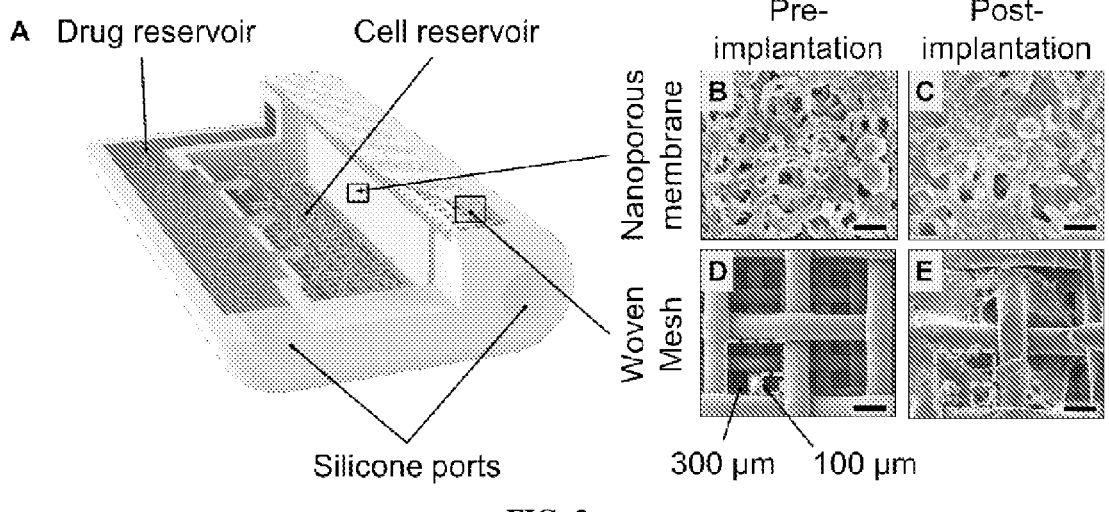
FIG. 2
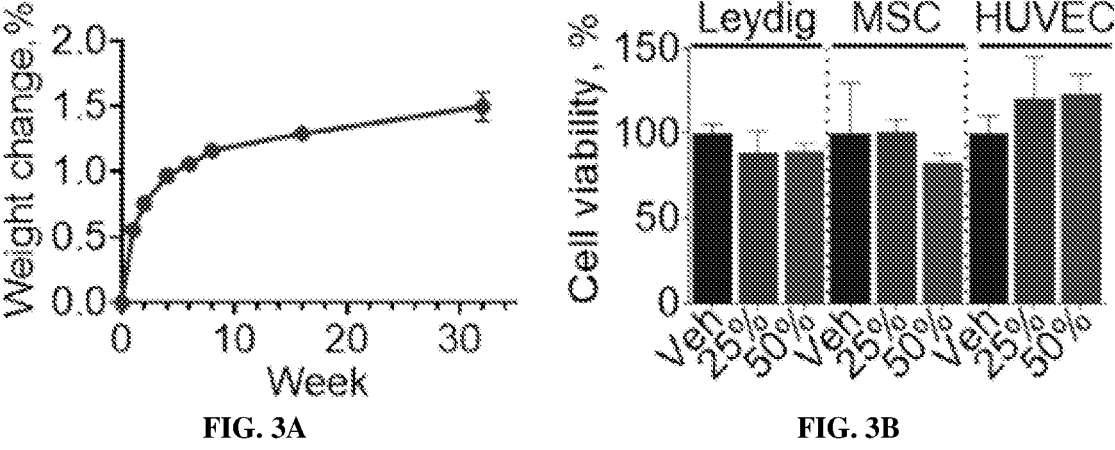
FIG. 3A                                    FIG. 3B

CTRL

MSC-250K

MSC-500K

DELIVERY DEVICES

CROSS-REFERENCE TO RELATED APPLICATIONS

This application claims the benefit of priority to U.S. Provisional Patent Application No. 63/043,439 filed Jun. 24, 2020, the disclosure of which is incorporated herein by reference in its entirety.

BACKGROUND

Cell therapy is a promising strategy for treatment of chronic diseases in which living, functional cells produce therapeutic factors in lieu of exogenous drug administration. To promote successful engraftment, survival, and functionality, cells require an optimal and protected environment that provides oxygen, nutrients, and cell-specific trophic factors such as growth factors, cytokines, hormones, and/or immune modulators. Importantly, long term cell survival may require that the trophic factors vary and remain confined throughout the lifespan of the graft. A promising approach to consolidate all these components into one environment is through cell encapsulation. However, cell encapsulation still faces the challenge of providing sufficient support for oxygen and nutrient transfer while maintaining versatile long-term administration of trophic factors.

Therapeutic vaccines have shown promise in the clinic for a variety of indications including cancer and autoimmune disease management. However, poor localization due to bolus injection leads to low and transient vaccine levels, which reduces the duration of antigen presentation and thus limits efficacy. As such, repeated administration is required to maintain a robust immune response over time. Numerous technologies are under development to WDVAX developed by Mooney and colleagues and licensed by Novartis for commercial use, are currently under clinical investigation to deliver vaccine components in melanoma patients. However, once implanted, vaccine components in these biomaterial-based scaffolds cannot be retrieved, modified or tuned according to a patient's response.

The present disclosure, including materials, devices and methods disclosed herein, address this and other needs.

SUMMARY

In accordance with the purposes of the disclosed devices, systems and methods as embodied and broadly described herein, the disclosed subject matter related to devices and systems, methods of making said devices and systems, and methods of using said devices and systems. More specifically, a device is provided comprising: a housing comprising a perimeter wall defining a cavity; and a support structure separating the cavity into a cell chamber and a reservoir chamber, the support structure comprises a porous membrane for fluid communication between the cell chamber and the reservoir chamber; wherein the cell chamber has an outside surface that comprises at least one mesh layer; and wherein the outside surface of the cell chamber comprises at least 50% of the total outside surface of the device.

In some embodiments, each mesh layer comprises a plurality of openings. In some embodiments, the plurality of openings has an average opening size that facilitates the growth of vascular tissue into the cell chamber. In some embodiments, the plurality of openings has an average opening size that prevents infiltration of immune cells into the cell chamber. In some embodiments, the plurality of openings has an average opening size that allows infiltration of immune cells into the cell chamber. In some embodiments, the plurality of openings has an average opening size ranging from about 50 microns to about 500 microns.

In some embodiments, the outside surface of the of the cell chamber comprises one mesh layer. In some embodiments, the outside surface of the cell chamber comprises a first mesh layer and a second mesh layer. In some embodiments, each of the first mesh layer and the second mesh layer has a plurality of openings. In some embodiments the plurality of openings for the first mesh layer has an average opening size of about 100 microns. In some embodiments, the plurality of openings for the second mesh layer has an average opening size of about 300 microns.

In some embodiments, the at least one mesh layer is derived from a polymeric material, for example nylon.

In some embodiments, the porous membrane comprises a nanoporous membrane. In some embodiments, the nanoporous membrane has a porosity ranging from about 2 nm to about 1000 nm. In some embodiments, the porous membrane comprises a nano-channel membrane having nano-channels with an average diameter ranging from about 2 nm to about 1000 nm.

In some embodiments, the housing is derived from a polymeric material, for example nylon.

In some embodiments, the cell chamber comprises a cell population, for example pancreatic islet cells, Leydig cells, follicular cells, stem cells, dendritic cells, stem cell-derived β-cells, genetically engineered cells, or combinations thereof. In some embodiments, the cell chamber comprises a cell lysate, for example a tumor cell lysate. In some embodiments, the cell chamber comprises one or more antigens.

In some embodiments, the reservoir chamber comprises one or more bioactive agents. In some embodiments, the reservoir chamber comprises one or more trophic factors. In some embodiments, the one or more trophic factors comprise one or more growth factors, for example vascular endothelial growth factor (VEGF), fibroblast growth factor (FGF), and angiopoietins. In some embodiments, the one or more trophic factors comprise one or more cytokines, for example lymphokines, interleukins, and chemokines. In some embodiments, the one or more trophic factors comprise one or more immunomodulators, for example Cytotoxic T-Lymphocyte-Associated Protein 4-Immunoglobulin Fusion Protein (CTLA4Ig), Y27632, FTY720, or deoxyspergualin (DSG). In some embodiments, the reservoir chamber comprises one or more immune adjuvants.

In another aspect, a device is provided comprising: a housing comprising a perimeter wall defining a cavity; and a support structure separating the cavity into a cell chamber and a reservoir chamber; wherein the cell chamber comprises a cell population and vascularized tissue; wherein the reservoir chamber comprises one or more trophic factors; wherein the support structure comprises a membrane configured to homogenously deliver the one or more trophic factors to the cell population in the cell chamber; wherein the cell chamber has an outside surface that comprises at least one mesh layer; and wherein the outside surface of the cell chamber comprises at least 50% of the total outside surface of the device.

In yet another aspect, a device is provided comprising: a housing comprising a perimeter wall defining a cavity; and a support structuring separating the cavity into a cell chamber and a reservoir chamber; wherein the cell chamber comprises a cell population, one or more antigens, and vascularized tissue; wherein the reservoir chamber comprises one or more immune adjuvants; wherein the support structure comprises a membrane configured to homogenously deliver the one or more immune adjuvants to the cell population; wherein the cell chamber has an outside surface that comprises at least one mesh layer; and wherein the outside surface of the cell chamber comprises at least 50% of the total outside surface of the device. In some embodiments, the cell population comprises an immune cell population.

In another aspect, a method of treating diabetes in a subject is provided, comprising: implanting a device as described herein in the subject, incubating the device until the device is infiltrated with vascular tissues; and injecting insulin producing cells into the cell chamber of the devices. In some embodiments, the method further comprises injecting an immunosuppressant into the reservoir chamber of the device.

In another aspect, a method of treating cancer in a tumor in a subject is provided, comprising: implanting a device as claimed herein in the subject; and injecting a cell lysate from a population of cells from the cancer into the cell chamber of the device. In some embodiments, the method further comprises injecting an immune adjuvant into the reservoir chamber of the device.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

(FIG. 1A) Mesenchymal stem cell hydrogen-filled NICHE is implanted in a subcutaneous pocket to stimulate vascularization. (FIG. 1B) Pre-vascularization phase, with blood vessel penetration into the cell reservoir. (FIG. 1C) Transcutaneous loading of immunosuppressant into NICHE drug reservoir. (FIG. 1D) Transcutaneous transplantation of cells into the vascularized and immunosuppressed cell reservoir.

FIG. 2 depicts an exemplary NICHE design. (A) Rendering of NICHE showing the cell and drug reservoir as well as the loading ports. SEM image of nylon nanoporous membrane before (B) and after (C) implantation. Scale bars represent 1 μm. SEM image of the two-layer nylon woven mesh before (D) and after (E) implantation. Scale bars represent 150 μm.

FIGS. 3A-3F depicts NICHE characterization and biocompatibility. (FIG. 3A) In vitro degradation test of NICHE structure. (FIG. 3B) Viability of Leydig cells, Mesenchymal Stem Cells (MSC), and Human Umbilical Vein Endothelial Cells (HUVEC) after incubation with NICHE extract. FFPE section of subcutaneous tissue in direct contact with NICHE at 10 weeks post-implantation stained with (FIG. 3C) Hematoxylin and Eosin (H&E) and (FIG. 3D) Masson's Trichrome (MT). Dotted line indicates NICHE-SC tissue intersection. (FIG. 3E) Poly-methyl methacrylate embedded sections of NICHE implanted for 10 weeks stained with H&E. Square indicates area of the fibrotic capsule magnified and stained with (FIG. 3F) MT. FFPE: Formalin-fixed, paraffin embedded; SC: subcutaneous; FC: Fibrotic capsule; DR: drug reservoir.

250,000 MSC (MSC-250K) or (FIG. 4C) 500,000 MSCs (MSC-500K) loaded in the cell reservoir. (FIG. 4D) Magnification of MSC-500K NICHE with visible blood vessels penetration from the subcutaneous tissue (black arrow) into the cell reservoir (white arrow). Representative H&E staining of FFPE sections of tissue collected from cell reservoirs of (FIG. 4E) CTRL, (FIG. 4F) MSC-250K, and (FIG. 4G) MSC-500K NICHE at 6 weeks post-implantation. Black arrows indicate blood vessels. (FIG. 4H) Blood vessel quantification per field of view of sections obtained from CTRL, MSC-250K, and MSC-500K NICHE (4 fields of view/slide; n-4-5 NICHE/condition). Results are mean±SD. Statistical analysis performed via one-way ANOVA; *p<0.05 and ***p<0.001. Immunofluorescence analysis of cell reservoir tissue collected from MSC-500K NICHE and immunostained for (FIG. 4I) aSMA and (FIG. 4J) RECA1. (FIG. 4K) Merged immunofluorescence image of aSMA-RECA1. (FIG. 4L) Magnification of area in K enclosed in the white square showing concentric labeling of aSMA-RECA1 in a blood vessel. MSC: Mesenchymal Stem Cells; H&E: Hematoxylin and Eosin; FFPE: Formalin-fixed, paraffin-embedded; aSMA: alpha smooth muscle actin; RECA1: Rat Endothelial Cell Antigen 1.

(FIG. 5F) Viability of Leydig cells and MSCs cultured with CTLA4Ig or culture media (Veh). (FIG. 5G) IVIS analysis of drug reservoir refilling in implanted NICHE using fluorescently tagged CTLA4Ig.

(FIG. 6A) IVIS analysis of allogeneic Leydig cells transplanted in NICHE receiving no immunosuppressive treatment (CTRL), local CTLA4Ig delivery from the drug reservoir (NICHE) or systemic CTLA4Ig delivery via intraperitoneal injections (IP). (FIG. 6B) IVIS signal intensity quantification relative to day of transplant. (FIG. 6C) Kaplan-Meier survival curve indicating last day of signal obtained from IVIS. Log-rank test NICHE vs IP p=0.65; NICHE vs CTRL p=0.005; IP vs CTRL p=0.01. (FIG. 6D) ELISA analysis of plasma CTLA4Ig concentration during the 31-day study. CTLA4Ig quantification in (FIG. 6E) transplant site: cell reservoir, fibrotic capsule, and skin in contact with NICHE or (FIG. 6F) peripheral organs at time of NICHE retrieval via ELISA. (FIG. 6G) CTLA4Ig quantification in tissue from cell reservoirs of viable and rejected grafts. PE: Post explant; Cell Res: Cell reservoir; FC: Fibrotic Capsule; Rej: Rejected. Mean±SD. Statistical analysis was performed via two-way ANOVA (D-F) and student's t-test (G). * p<0.05, *** p<0.001.

(FIG. 7A) Rejected grafts in NICHE local immunosuppression cohort, (FIG. 7B) 3× magnification of white box in A. (FIG. 7C) Viable grafts under NICHE local immunosuppression, (FIG. 7D) 3× magnification of white box in C. (FIG. 7E) Viable grafts under systemic IP immunosuppression, (FIG. 7F) 3× magnification of white box in E.

(FIG. 8C) Blood vessels branching inside the cell reservoir.

(FIG. 15A) cytokine loading into nanolymph prior to (FIG. 15B) subcutaneous implantation near tumor site. Cytokine diffusion recruits DCs to nanolymph vicinity. (FIG. 15C) Transcutaneous filling of antigen-carrying tumor lysate. (FIG. 15D) Recruits DCs are activated against tumor antigens.

Like reference symbols in the various drawings indicate like elements.

DETAILED DESCRIPTION

Figure 1A:
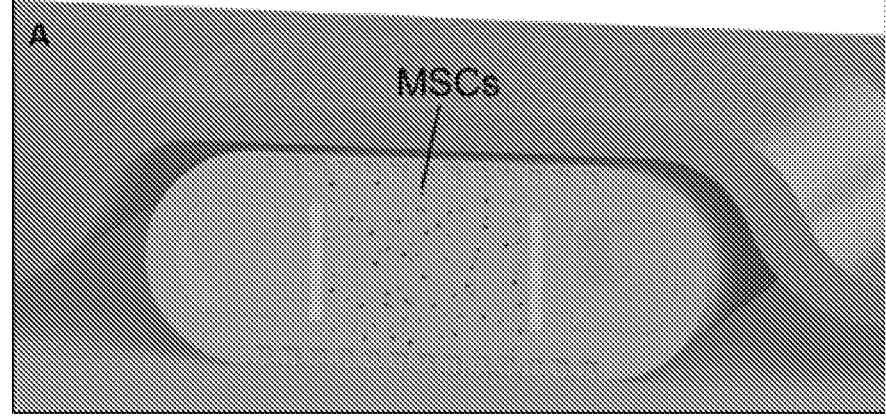
FIGS. 1A-1D depicts the Neovascularized Implantable Cell Homing Encapsulation (NICHE) deployment strategy.

Many modifications and other embodiments disclosed herein will come to mind to one skilled in the art to which the disclosed devices, systems and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from and combined with the features of any of the other several embodiments without departing from the scope or spirit of the present disclosure.

Any recited method can be carried out in the order of events recited or in any other order that is logically possible. That is, unless otherwise expressly stated, it is no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operations flow, plain meaning derived from grammatical organization or punctuation, or the number or type of aspects described in the specification.

All publications mentioned herein are incorporated by reference to disclose and described the methods and/or materials in connection with which the publications are cited. The publications discussed herein are provided solely for their disclosure prior to the filing date of the present application.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed devices, systems, and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

As used herein, "comprising" is to be interpreted as specifying the present of the stated features, integers, steps, or components as referred to, but does not preclude the present or addition of one or more features, integers, steps, or components, or groups thereof. Moreover, each of the terms "by", "comprising", "comprises", "comprised of", "including", "includes", "included", "involving", "involves", "involved", and "such as" are used in their open, non-limiting sense and may be used interchangeably. Further, the term "comprising" is intended to include examples and aspects encompassed by the terms "consisting essentially of" and "consisting of". Similarly, the term "consisting essentially of" is intended to include examples encompassed by the term "consisting of".

As used in the specification and the appended claims, the singular forms "a", "an" and "the" include plural referents unless the context clearly dictates otherwise.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about another particular value. Similarly, when values are expressed as approximations, by use of the antecedent "about", it will be understood that the particular value forms a further aspect. For example, if the value "about 10" is disclosed, then "10" is also disclosed.

When a range is expressed, a further aspect includes from the one particular value and/or to the other particular value. For example, when the stated range include one or both of the limits, ranges excluding either or both of those included limits are also included in the disclosure, e.g., the phrase "x to y" include the range from "x" to "y" as well as the range greater than "x" and less than "y". The range can also be expressed as an upper limit, e.g., "about x, y, s, or less" and should be to include the specific ranges "about x", "about y" and "about z" as well as the ranges "less than x", "less than y", and "less than z". Likewise, the phrase "about x, y, z or greater" should be interpreted to include the specific ranges of "about x", "about y", and "about z" as well as the ranges "greater than x", "greater than y", and "greater than z". In addition, the phrase "about x to y", wherein "x" and "y" are numerical values, includes "about x to about y".

It is understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also includes individual values (e.g., about 1%, about 2%, about 3%, and about 4%) and the sub-ranges (e.g., about 0.5% to about 1.1%, about 0.5% to about 2.5%, about 0.5% to about 3.2%, about 0.5% to about 4.4%, and other possible sub-ranges) within the indicated range.

As used herein, the terms "about", "approximate", "at or about", and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art that equivalent results or effects are obtained.

In some circumstances, the value that provides equivalent results or effects cannot be reasonably be determined. In such cases, it is generally understood, as used herein, that "about or "at or about" mean the nominal value indicated±10% variation unless otherwise indicated or inferred. In general, an amount, size, formulation, parameter, or other quantity or characteristic is "about", "approximate", or "at or about" whether or not expressly stated to be such. It is understood that where "about", "approximate", or "at or about" is used before a quantitative value, the parameter also includes the specific quantitative value itself, unless specifically stated otherwise.

As used herein, the term "device" is intended to encompass a product comprising the specified components, as well as any product which results, directly or indirectly, from combination of the specified components in the specified amounts.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/ or physiological effect. The effect can be, but does not necessarily have to be, prophylactic in terms of preventing or partially preventing a disease, symptom or condition thereof, such as an ophthalmological disorder. The effect can be therapeutic in terms of a partial or complete cure of a disease, condition, symptom or adverse effect attributed to the disease, disorder, or condition. The term "treatment" as used herein can include any treatment of ophthalmological disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

Devices

In one aspect, a device is provided comprising:

a housing comprising a perimeter wall defining a cavity; and a support structure separating the cavity into a cell chamber and a reservoir chamber;

wherein the support structure comprises a porous membrane for fluid communication between the cell chamber and the reservoir chamber;

wherein the cell chamber has an outside surface that comprises at least one mesh layer; and wherein the outside surface of the cell chamber comprises at least 50% of the total outside surface of the device.

The device can have any configuration or shape appropriate for maintaining biological activity and providing access for delivery of a cell or function, including for example, cylindrical, rectangular, disc-shaped, square-shaped, ovoid, stellate, or spherical. Moreover, the device can be coiled or tubular. In cases where the device is to be retrieved at some time after it is implanted, configurations which tend to lead to migration of the devices from the site of implantation (such as spherical devices small enough to travel in the recipient's blood vessels) should be avoided. As noted herein, all or portions of the device can be formed from a 3D printer. Thus the shape can be highly complex and irregular, depending on the particular payload and location of use. Preferably, the device can be configured to offer high structural integrity and are easy to retrieve from the host. In some specific examples, the device is flexible so that it can be easily maneuvered (implanted and removed).

The dimensions of the device can be varied depending on the contents of the chambers, the volume of the chambers, the intended use, and the like. For example, the dimensions of the device can permit serial implantation throughout a tissue volume via a minimally-invasive, trocar delivery mechanism. The dimensions can also be established to fit into a specific location in a subject. There are no strict requirements for the device dimensions and can be ultimately tailored to match the size of commercially available deployment systems already adopted in clinics.

Figure 11:
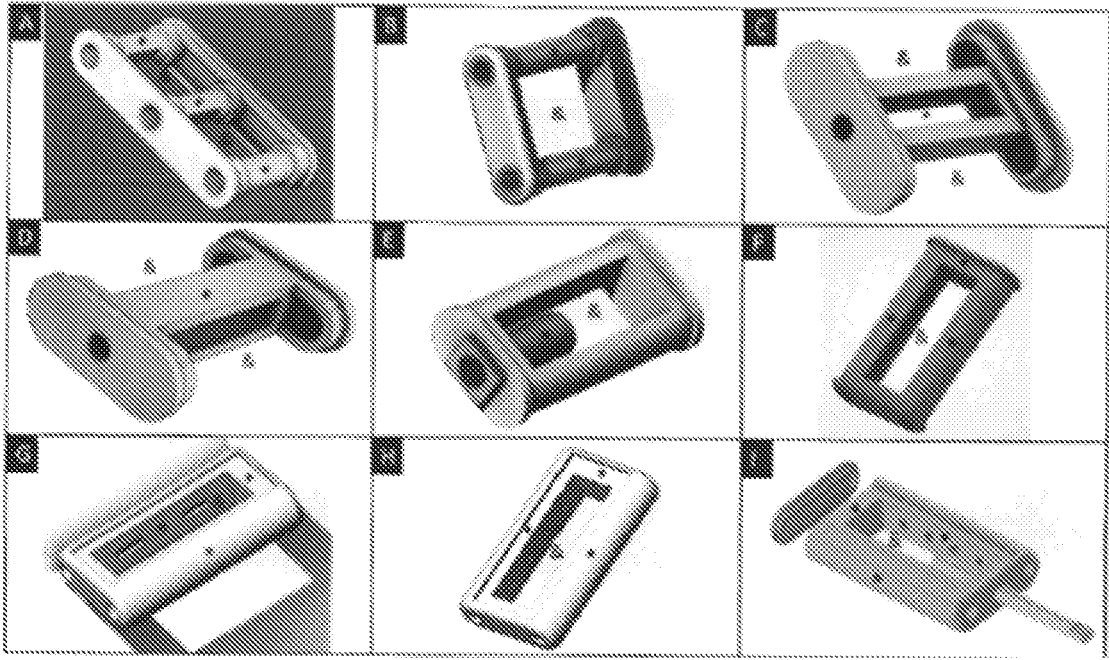
FIG. 11 depicts possible design iterations of the devices disclosed herein. * indicates the reservoir chamber; & indicates the cell chamber.

Non-limiting examples of device configurations are provided in FIG. 11, wherein * indicates the configuration of one or more reservoir chambers and & indicates the configuration of one or more cell chambers. In panel A of FIG. 11, a representative device configuration is provided wherein the reservoir chamber comprises 3 tubes with a window covered by the porous membrane; the structure is then wrapped in at least one mesh layer to define the cell chamber. In panel B of FIG. 11, a representative device configuration is provided wherein the reservoir chamber is the same as that provided in panel A but wherein the tubes are connected by a channel along one section of the structure. In panels C and D of FIG. 11, representative device configurations are provided wherein the reservoir chamber is centrally located within the structure which is then wrapped with at least one mesh layer to define the cell chamber. In panel E of FIG. 11, a representative device configuration is provided wherein the reservoir chamber is removeable and replaceable. In panels F, G, and H of FIG. 11, representative device configurations are provided wherein the reservoir chamber is U-shaped, i.e. the reservoir chamber surrounds the cell chamber on three sides. In panel I of FIG. 11, a representative device configuration is provided similar to that of panels F-H, but further comprising a cylindrical cell spacer to reduce pressure on any transplanted cells within the cell chamber.

In some embodiments, the device may have a longest linear dimension of less than 60 mm, e.g. less than 50 mm, less than 40 mm, less than 30 mm, less than 25 mm, less than 20 mm, or less than 15 mm. In some embodiments, the device may have a longest linear dimension of greater than 10 mm, for example greater than 20 mm, greater than 30 mm, greater than 40 mm, or greater than 50 mm.

Housing

The housing (body) of the device can be fabricated from a material that is biologically acceptable, e.g., does not illicit an immune response. Various polymers and polymer blends can be used to manufacture the device, including, biodegradable or non-biodegradable materials. The device housing is preferably fabricated from a hydrophilic, viscoelastic, and/or biocompatible material. However, other materials can be used to fabricate the device and the surface of the device subsequently surface treated with a material that is hydrophilic, viscoelastic, and/or biocompatible. In specific examples, the device is surface treated with a biomaterials.

Examples of suitable polymers for fabricating the device include polylactic acids (PLA), polyalkylenes (including polypropylene and polyethylene), poly(alkylene glycols), polycarbonate (PC), cyclic olefin polymer (COP), poly(trimethylene carbonate), polycaprolactone (PCL), poly(lactic-co-glycolic acid) (PLGA), polyacrylates (including acrylic copolymers), polyacrylonitrile, polyvinylidenes, polyvinyl chloride copolymers, polyurethanes, polystyrenes, polyimides, polyamides, polyethyleneimine, cellulose polymers (including cellulose acetates and cellulose nitrates), polysulfones (including polyethersulfones), polyesters, polyphosphazenes, polyacrylonitriles, poly(acrylonitrile-co-vinylchloride), poly(vinylsiloxane), as well as derivatives, copolymers, and mixtures of the foregoing. Additional examples that may be used include tetrafluoroethylene/polytetrafluoroethylene (PTFE), ePTFE (expanded polytetrafluoroethylene), hydroxypropyl methyl cellulose (HMPC), methacrylate polymers, poly(ethylene glycol), poly(ethyl ethacrylate), polyhydroxyvalerate, polyhydroxybutyrate, polydioxanone, polyanhydrides, polycyanocrylates, poly(amino acids), poly(orthoesters), copolymers of polyalkylene glycols, terephthalates, collagen, gelatin, chitosan, fibronectin, extracellular matrix proteins, vinculin, agar, agarose, and alginates, or combinations thereof.

In particular embodiments, the housing is derived from a polyamide (i.e., a nylon).

Cell Chamber

As described herein, the devices can include a cell chamber for housing transplanted or recruited cells. The cell chamber has an outside surface that comprises at least one mesh layer. The at least one mesh layer can be of a "semi-permeable" nature to permit, for example, molecules produced by cells within the cell chamber to diffuse from the device into the surrounding host tissue, as well as for vascular tissue to grow into the first chamber.

In some embodiments, the cell chamber may have a length in the longest linear direction ranging from about 5 mm to about 50 mm, for example a length of about 5 mm, about 10 mm, about 15 mm, about 20 mm, about 25 mm, about 30 mm, about 35 mm, about 40 mm, about 45 mm, or about 50 mm.

In some embodiments, the cell chamber may have an interior volume ranging from about 50 $mm^3$ to about 5000 $mm^3$, for example an interior volume of about 50 $mm^3$, 100 $mm^3$, about 200 $mm^3$, about 300 $mm^3$, about 400 $mm^3$, about 500 $mm^3$, about 600 $mm^3$, about 700 $mm^3$, about 800 $mm^3$, about 900 $mm^3$, about 1000 $mm^3$, about 1100 $mm^3$, about 1200 $mm^3$, about 1300 $mm^3$, about 1400 $mm^3$, about 1500 $mm^3$, about 1600 $mm^3$, about 1700 $mm^3$, about 1800 $mm^3$, about 1900 $mm^3$, about 2000 $mm^3$, about 2100 $mm^3$, about 2200 $mm^3$, about 2300 $mm^3$, about 2400 $mm^3$, about 2500 $mm^3$, about 2600 $mm^3$, about 2700 $mm^3$, about 2800 $mm^3$, about 2900 $mm^3$, about 3000 $mm^3$, about 3100 $mm^3$, about 3200 $mm^3$, about 3300 $mm^3$, about 3400 $mm^3$, about 3500 $mm^3$, about 3600 $mm^3$, about 3700 $mm^3$, about 3800 $mm^3$, about 3900 $mm^3$, about 4000 $mm^3$, about 4100 $mm^3$, about 4200 $mm^3$, about 4300 $mm^3$, about 4400 $mm^3$, about 4500 $mm^3$, about 4600 $mm^3$, about 4700 $mm^3$, about 4800 $mm^3$, about 4900 $mm^3$, or about 5000 $mm^3$.

In another aspect, the cell reservoir has an outside surface that comes into contact with the tissue of the host when implanted. In typical embodiments, the outside surface of the cell reservoir comprises at least 50%, at least 60%, at least 70% or more of the total surface of the device that comes into contact with the tissue of the host when implanted.

In one aspect, the outside surface of the cell reservoir comprises at least one mesh layer having a plurality of openings. In some embodiments, particularly in those where the cell reservoir is to house a cell population, each opening is of such a size to allow micro-vessels (for example, transmembrane blood vessels) to enter the device and be maintained as robust, health vessels, which is important for the survival and normal functioning of the cell population housed within the cell reservoir. In other embodiments, particularly in those where the cell reservoir is used to house one or more antigens, each opening is of such a size to allow infiltration of immune cells from the host, for example allowing infiltration of host dendritic cells (DC).

The average size of each opening in the plurality of openings in the at least one mesh layer can independently range for each mesh layer from about 2 microns to about 500 microns, for example from about 50 to about 500 microns, from about 100 to about 500 microns, from about 200 to about 500 microns, from about 300 to about 500 microns, from about 400 to about 500 microns, from about 2 to about 400 microns, from about 50 to about 400 microns, from about 100 to about 400 microns, from about 200 to 400 microns, from about 300 to about 400 microns, from about 2 to about 300 microns, from about 50 to about 300 microns, from about 100 to about 300 microns, from about 200 to about 300 microns, from about 2 to about 200 microns, from about 50 to about 200 microns, from about 100 to about 200 microns, from about 2 to about 100 microns, from about 50 to about 100 microns, or from about 2 to about 50 microns. In some embodiments, the average size of each opening in the plurality of openings in the at least one mesh layer can be, independently for each mesh layer, about 2 microns, about 10 microns, about 20 microns, about 30 microns, about 40 microns, about 50 microns, about 60 microns, about 70 microns, about 80 microns, about 90 microns, about 100 microns, about 110 microns, about 120 microns, about 130 microns, about 140 microns, about 150 microns, about 160 microns, about 170 microns, about 180 microns, about 190 microns, about 200 microns, about 210 microns, about 220 microns, about 230 microns, about 240 microns, about 250 microns, about 260 microns, about 270 microns, about 280 microns, about 290 microns, about 300 microns, about 310 microns, about 320 microns, about 330 microns, about 340 microns, about 350 microns, about 360 microns, about 370 microns, about 380 microns, about 390 microns, about 400 microns, about 410 microns, about 420 microns, about 430 microns, about 440 microns, about 450 microns, about 460 microns, about 470 microns, about 480 microns, about 490 microns, or about 500 microns.

In some embodiments, the outside surface of the cell reservoir comprises one mesh layer. In some embodiments, the outside surface of the cell reservoir comprises two mesh layers, where each mesh layer has a plurality of openings of different size. In some embodiments, the outside surface of the cell reservoir comprises a first mesh layer and a second mesh layer, wherein the average size of each opening in the plurality of openings in the first mesh layer is about 100 microns and the average size of each opening in the plurality of openings in the second mesh layer is about 300 microns.

In some embodiments, the at least one mesh layer may be fabricated from a material that is biologically acceptable, e.g., does not illicit an immune response. The at least one mesh layer may comprise the same material as the housing of the device or may be formed from a different material. In particular embodiments, the at least one mesh layer may comprise a polyamide (i.e., nylon).

The cell chamber can include a loading port for loading of the desired payload into the chamber. The loading port can be included in the at least one mesh layer or as part of the device itself. The loading port can be on top or the side of the device. In some embodiments, the loading port can be an opening sealed with a plastic, rubber, or silicone. The payload can be filled into the cell chamber through the loading port and then sealed. In some embodiments, the size of the loading port can be from 0.5 mm to 3 mm, from 0.5 mm to 2 mm, or from 1 mm to 2 mm.

The cell chamber can further comprise a biological or non-biological agent to stimulate tissue incorporation and angiogenesis, for example, growth factors. Examples of biological or non-biological agents to stimulate tissue incorporation and angiogenesis include but are not limited to: VEGF, PDGF, FGF1, NRP1, Ang1, Ang2, TGFβ/endoglin, MCP1, αvβ5, αvβ5, CD31, VE-cadherin, ephrin, plasminogen activators, angiogenenin, Dell, aFGF, vFGF, follistatin, GCSF, HGF, 118, leptin, midkine, placental growth factor, PDECGF, PTN, progranulin, proliferin, TGFα, and TNFα. In some embodiments, the biological agent to stimulate tissue incorporation and angiogenesis may comprise mesenchymal stem cells.

In some embodiments, the cell chamber may further comprise one or more antigens. In some embodiments, the cell chamber may further comprise a cell lysate, for example a tumor lysate.

In some embodiments, the devices described herein may contain two or more cell chambers, for example two, three, four, or more chambers.

Reservoir Chamber

As described herein, the device can include a reservoir chamber. The reservoir chamber can be used as a bioactive delivery vehicle. For example, a major challenge in transplantation is the induction of donor specific tolerance. A localized delivery of immunomodulatory drugs in the vicinity of transplanted tissue, which will protect the transplant from immune reaction and at the same time eliminate the adverse effects associated with systemic immunosuppression, is the choice in cell transplantation. The disclosed reservoir chamber can be configured to provide a constant and sustained delivery of bioactives, for example immunomodulatory drugs, to any cells present within the cell chamber.

The size of the reservoir chamber can be varied depending on the contents of the reservoir chamber, the volume of the reservoir chamber, the intended use, and the like. In some embodiments, the reservoir chamber can hold a volume ranging from about 50 μL to about 3500 μL, for example a volume of about 50 μL, about 100 μL, about 200 μL, about 300 μL, about 400 μL, about 500 μL, about 600 μL, about 700 μL, about 800 μL, about 900 μL, about 1000 μL, about 1250 μL, about 1500 μL, about 1750 μL, about 2000 μL, about 2250 μL, about 2500 μL, about 2750 μL, about 3000 μL, about 3250 μL, or about 2500 μL. In some embodiments, the reservoir chamber can hold a volume ranging from about 50 μL to about 3500 μL, from about 100 μL to about 3500 μL, from about 500 μL to about 3500 μL, from about 1000 μL to about 3500 μL, from about 1500 μL to about 3500 μL, from about 2000 μL to about 3500 μL, from about 2500 μL to about 3500 μL, from about 3000 μL to about 3500 μL, from about 50 μL to about 3000 μL, from about 100 μL to about 3000 μL, from about 500 μL to about 3000 μL, from about 1000 μL to about 3000 μL, from about 1500 μL to about 3000 μL, from about 2000 μL to about 3000 μL, from about 2500 μL to about 3000 μL, from about 50 μL to about 2500 μL, from about 100 μL to about 2500 μL, from about 500 μL to about 2500 μL, from about 1000 μL to about 2500 μL, from about 1500 μL to about 2500 μL, from about 2000 μL to about 2500 μL, from about 50 μL to about 2000 μL, from about 100 μL to about 2000 μL, from about 500 μL to about 2000 μL, from about 1000 μL to about 2000 μL, from about 1500 μL to about 2000 μL, from about 50 μL to about 1500 μL, from about 100 μL to about 1500 μL, from about 500 μL to about 1500 μL, from about 1000 μL to about 1500 μL, from about 50 μL to about 1000 μL, from about 100 μL to about 1000 μL, from about 500 μL to about 1000 μL, from about 50 μL to about 500 μL, from about 100 μL to about 500 μL, or from about 50 μL to about 100 μL.

In some embodiments, the reservoir chamber may be U-shaped, i.e. the reservoir chamber surrounds the cell chamber on three sides.

The reservoir chamber can also comprise one or more loading ports for loading of material to be housed within the reservoir chamber. In some examples, the loading port can be accessed through the skin of the host. The reservoir chamber is not vascularized and is free from tissue. In some embodiments, the loading port can be made of materials that are penetrable with a medical needle and resealable after penetration. Such materials include plastic, rubber, or silicone. The payload can be filled into the reservoir chamber through the loading port and then sealed. In some embodiments, the size of the loading port can be from 0.5 mm to 3 mm, from 0.5 mm to 2 mm, or from 1 mm to 2 mm.

In some embodiments, the reservoir chamber can contain a payload with a dosage designed for a specific purpose. Useful dosages of compounds, agents, and/or pharmaceutical compositions useful with the devices disclosed herein can be determined by those skilled in the art, for example, by comparing their in vitro activity and in vivo activity in animal models. Methods for extrapolation of effective dosages in mice, and other animals, to humans are known in the art; for example, see U.S. Pat. No. 4,938,949.

In some embodiments, the reservoir chamber may contain one or more trophic factors. The one or more trophic factors may comprise growth factors, cytokines, or immunomodulators.

Growth factors which may be used in the reservoir chamber include, but are not limited to, transforming growth factor α (TGF-α), transforming growth factor-β (TGF-β) including β, β1, β2, and β3, platelet-derived growth factor (PDGF), fibroblast growth factors (FGF), including FGF acidic isoforms 1 and 2, GF basic form 2 and FGF 4, 8, 9, and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factors (IGF) including IGF I and II, vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), skeletal growth factor, bone matrix derived growth factor, and bone derived growth factors.

Cytokines which may be used in the reservoir chamber include, but are not limited to, cardiotrophin, stromal cell derived factor, macrophage derived chemokine (MC), melanoma growth stimulatory activity (MGSA), macrophage inflammatory proteins (MIP) including 1α, 2, 3α, 3β, 4, and 5, IL-1, IL-2, IL-3, IL-4, IL-5, IL-6, IL-7, IL-8, IL-9, IL-10, IL-11, IL-12, IL-13, TNF-α, and TNF-β.

Immunomodulatory agents which may be used in the reservoir chamber include, but are not limited to, corticosteroids, cytostatics, calcineurin inhibitors, and some antibodies; for example antibodies such as anti-thymocyte globulin, anti-thymocyte globulin, and PF-06823859; antisense oligonucleotides such as alicaforsen sodium, ATL-1102, and QPI-1002; aptamers such as emapticap pegol and olaptesed pegol; bispecific monoclonal antibodies such as MaaT-013; blood derivatives such as SAR-156597 and albumin; fusion proteins such as alpha-1 proteinase inhibitor, etanercept, abatacept, rilonacept, belatacept, alefacept, SL-401, atacicept, RCT-18, CD-24Fc, F-652, RSLV-132, MDNA-55, and T-Guard; monoclonal antibodies such as adalimumab, infliximab, ustekinumab, eculizumab, golimumab, natalizumab, tocilizumab, certolizumab pegol, vedolizumab, secukinumab, lemtrada, belimumab, canakinumab, obinutuzumab, ixekizumab, daclizumab, alemtuzumab, ocrelizumab, tildrakizumab, siltuximab, brodalumab, basiliximab, ABCream, reslizumab, muromonab-CD3, dupilumab, efalizumab, sarilumab, guselkumab, risankizumab, emapalumab, ravulizumab, xilonix, OMS-721, BI-655130, mirikizumab, ozoralizumab, leronlimab, ianalumab, bimekizumab, infliximab biobetter, ocaratuzumab, tralokinumab, inolimomab, olokizumab, anifrolumab, belimumab+rituximab, BCD-085, basiliximab biobetter, BIVV-009, RG-6107, IFX-1, talacotuzumab, namilumab, otelixizumab, bleselumab, BT-063, foralumab, SAL-021, monoclonal antibody to antagonize IL-2R beta for celiac disease, oncology and tropical spastic paraparesis, vobarilizumab, brazikumab, KHK-4083, GBR-830, CNTO-6785, clazakizumab, lebrikizumab, (dectrekumab+VAK-694), orilanolimab, RPC-4046, REGN-3500, iscalimab, prezalumab, sirukumab, BOS-161721, BCD-089, dapirolizumab pegol, AMG-714, siplizumab, BIIB-059, monoclonal antibody to inhibit TNF-alpha for musculoskeletal disorders, MOR-106, OPN-305, BMS-986253, GSK-2330811, rozanolixizumab, CJM-112, KPL-301, etokimab, and ANB-019; oligonucleotides such as defibrotide sodium; polysaccharides such as dociparstat sodium; proteins such as CI esterase inhibitor, bee venom, ARG-201, and PRTX-100; recombinant enzymes such as imlifidase; recombinant proteins such as anakinra, CI esterase inhibitor (recombinant), tadekinig alfa, nomacopan, sanguinate, dekavil, ABY-035, INV-103, and tiprelestat; small molecules such as lenalidomide, fingolimod hydrochloride, tacrolimus, sildenafil citrate, teriflunomide, pomalidomide, apremilast, tofacitinib citrate, pirfenidone, ambrisentan, mycophenolate mofetil, bendamustine hydrochloride, cyclosporine, zortress, mycophenolate sodium DR, sirolimus, thalidomide, mizoribine, tranilast, methotrexate, hydrocortisone, panobinostat, maxtrex, leflunomide, tofacitinib citrate ER, icosapent ethyl, cladribine, baricitinib, gusperimus trihydrochloride, amifampridine phosphate, sonidegib phosphate, tacrolimus ER, mizoribine ODT, lefluonomide, methoxsalen, azathioprine, rofecoxib, avacopan, glasdegib, peficitinib hydrobromide, ozanimod hydrochloride, AC-203, brimonidine tartrate, reproxalap, voclosporin, BMS-986165, abrocitinib, delgocitinib, ponesimod, cenicriviroc, seletalisib, reparixin, BB-3, leniolisib, epinephrine, ACT-774312, didox, LC-280126, VB-201, IBsolvMIR, cyclosporine CR, PF-06650833 MR, lipidated tacrolimus, KZR-616, AS-101, CC-11050, JTE-051, entospletinib, cannabidiol, PRN-1008, grapiprant, hydroxytriptolide, PF-06700841, PF-06651600, laquinimod sodium, sotrastaurin acetate, KD-025, emricasan, RGI-2001, diacerein, spebrutinib besylate, cerdulatinib, ubidecarenone, NC-2400, AKP-11, arsenic trioxide, poseltinib, GKT-831, levalbuterol sulfate, ladarixin, cenerimod, iberdomide hydrochloride, diacerein CR, GS-9876, RG-7625, evobrutinib, YRA-1909, and forigerimod acetate; synthetic peptides such as APL-2, ampion, RGN-259, brimapitide, cibinetide, CBLB-612, BNZ-1, and RA-101495; MT-7117; ICP-022, and Myadept.

In some embodiments, the reservoir chamber may comprise one or more immune adjuvants. Representative examples of immune adjuvants which may be used include, but are not limited to, adjuvants for cancer (e.g., GM-CSF, CpG ODN, imiquimod), for type 1 diabetes (e.g., beta islet cell proteins, GAD 65), for rheumatoid arthritis (e.g., type II collagen, gp39, dnajp1), for multiple sclerosis (e.g., myelin-based proteins) or for Alzheimer's disease (e.g., amyloid beta proteins, anti-amyloid beta targeting antibodies, TLR agonists).

In some embodiments, the devices described herein may contain two or more reservoir chambers, for example two, three, four, or more reservoir chambers.

Support Structure

The devices disclosed herein include a support structure separating the cell chamber and the reservoir chamber. The support structure need not provide structural support for the entire device or the housing (though it can); it need only provide support for the membrane between the reservoir chamber and the cell chamber.

In one aspect, the support structure can comprise a porous membrane. The membrane is of a "semi-permeable" nature to permit drugs, particles, and/or biomolecules, for example, to diffuse from the reservoir chamber to the cell chamber. Numerous variables can affect the pharmacokinetics of the drugs, particles, and/or biomolecules release. The membrane in preferred embodiments can be optimized for short- or long-term release. In some embodiments, the membrane is optimized for short-term release of drugs, particles, and/or biomolecules from the reservoir chamber to the cell chamber. In some embodiments, the membrane is optimized for long-term release of drugs, particles, and/or biomolecules from the reservoir chamber to the cell chamber. In some embodiments, the membrane can combine short-term and long-term release of drugs, particles, and/or biomolecules from the reservoir chamber to the cell chamber. As used herein, "controlled", "sustained", or "extended" release of the factors can be continuous or discontinuous, linear or non-linear. The porous membrane can be formed of steel, glass, synthetic or natural polymers, polystyrene, cellulose, glass, or any other material. The porous barrier can be affixed to the support structure by any means, for example welding, gluing, fusing, or any other method that allows for filtration. The porous membrane may be a nanoporous membrane, i.e. a membrane that has a porosity ranging from about 2.5 nm to about 1000 nm, for example, a porosity of about 2.5 nm, about 5 nm, about 10 nm, about 20 nm, about 25 nm, about 40 nm, about 50 nm, about 75 nm, about 100 nm, about 500 nm, about 750 nm, or about 1000 nm.

In some embodiments, the porous membrane can comprise a nano-channel membrane. Nano-channel membranes are described in PCT/US2016/032658, filed May 16, 2016, which is incorporated herein by reference in its entirety. Briefly, the nano-channel membrane can include hundreds of thousands of densely packed nano-channels with precisely controlled size and surface properties. At the nanoscale, molecular interactions with the channel wall dominate the transport of fluids to such an extent that the classical mechanical laws of diffusion (Fick's laws) break down. Thus, nanoscale phenomena are used herein to achieve the goal of constant release of the factors from the reservoir chamber over periods of time ranging from weeks to months and over a broad range of molecular sizes, at release rates relevant for medical applications. Constant and sustained release can be achieved with a large number of molecules ranging from small organic molecules to small molecular weight to large molecular weight peptides. In some embodiments, the nano-channel membrane can offer tightly-controlled release of drugs, particles, and/or biomolecules through its high spatial and electrostatic hindrance within its channels.

The nano-channels can be fabricated with varying height and channel density, enabling tuning to fit a given molecule and desired dose release rate. For example, the nanochannel membrane can have nano-channels having an average diameter ranging from about 2.5 nm to about 1000 nm in diameter, for example, the nanochannels can have an average diameter of about 2.5 nm, about 5 nm, about 10 nm, about 20 nm, about 25 nm, about 40 nm, about 50 nm, about 75 nm, about 100 nm, about 500 nm, about 750 nm, or about 1000 nm. The density of the nano-channels in the membrane can be at least about 50,000, at least about 100,00, or at least about 150,000 nanochannels per mm$^2$.

In general, it is desirable that diffusion of the factors across the membrane is homogenously and locally distributed to the cell chamber. To optimize local delivery to the cell chamber, the membrane can be micro-fabricated with photolithographic techniques from a polymer material, allow for fine control over channel size and distribution in the 20-1000 nm range. In the disclosed devices, the membrane can locally delivery a drug, particle, and/or biomolecule from the reservoir chamber to any cell present within the cell chamber.

Methods of Making

Methods for making the devices described herein are also disclosed. In certain embodiments, the device can be fabricated using a custom 3D printer technology. In some embodiments, the 3D printer can run on a fused deposition modeling (FDM) technique, building parts layer-by-layer from the bottom-up by heating and extruding thermoplastic filament. The 3D printer can alternatively run on a stereolithography (SLA) technique, building layers by focusing light onto a photopolymer. A solid modeling software (for example, SolidWorks™, Dassault Systems SolidWorks Corp.) can be used to create a 3D dataset for the fabrication process. In some instances, the housing can be fabricated using a custom 3D printer technology while the membrane can be fabricated as described in PCT/US2016/032658, filed May 16, 2016 (for example, through removal of atomic layer deposited tungsten (a sacrificial layer) by H$_2$O$_2$ etching). In another embodiment, the 3D printer can run on a selective laser sintering (SLS) technique.

After fabrication, the device can be surface modified as described herein to, for example, increase its hydrophilicity and obtain a suitable external charge. In specific examples, the surface of the device can be plasma treated. Plasma treatment can include immersing the device in a base such as 5 M NaOH followed by rinsing and drying. An argon plasma (Ar) or oxygen plasma (O$_2$) etching process can be carried out. Other methods of surface modification include attaching an endothelial cell attachment factor.

Methods of Use

Methods for using the devices are also disclosed herein. In some embodiments, the devices can be used for delivering cells into a human or non-human subject. The cell delivery method can be a multistep process comprising a device implantation step followed by a cell and optionally drug infusion step. In some embodiments, the method can include implanting a device as disclosed herein in the subject's body prior to delivery of the cells. The implanted device can be maintained in the host for an adequate time for collagen and blood vessels to infiltrate the micro-channels of the cell chamber. In some embodiments, the device can be sterilized using, for example, ethylene oxide, gamma radiation or dry heat autoclaving prior to implantation. The type of sterilization method used is dependent on the housing material, since dry heat autoclaving may warp certain polymeric materials (e.g., polypropylene) due to low heat deflection temperature.

The device can be implanted subcutaneously, percutaneously, transcutaneously, or intraperitoneally. For example, for subcutaneous implantation of the device in the subject, an incision can be made through the dermis and epidermis followed by careful blunt dissection of connective and adipose tissue, creating a subcutaneous pocket caudal to the incision line. Once an adequate space is created (roughly the dimensions of the device), the device can be implanted into the subcutaneous pocket, and the incision sutured. Alternatively, the device can be implanted in the peritoneal cavity through an abdominal incision. The device implantation steps can be followed by a device incubation period during which a vascularized matrix is deposited in and around the cell chamber.

After the incubation period, cells can be loaded transcutaneously through the port, without surgery when the device is implanted subcutaneously. If the device is implanted in certain deeper sites, access can be obtained via a second surgery (e.g., laparoscopic surgery). Delivery of a cellular preparation into the device can be made by using a cell delivery apparatus. The delivery apparatus (such as a syringe or cell infusion tube) can be loaded with the cellular preparation, and the syringe or tube can be inserted into the injection port of the cell chamber. When the device is completely filled with the cellular preparation, cell infusion can be stopped and the delivery device retracted from the device.

Prior to, during, or after delivery of the cellular preparation, the method can further include delivery of a drug preparation into the reservoir chamber. For delivery the drug preparation into the device, a delivery apparatus (such as a syringe) can be loaded with a drug preparation, and the apparatus can be inserted into the injection port of the reservoir chamber. When the device is completely filled with the drug preparation, drug infusion can be stopped and the delivery apparatus retracted from the device. The injection port can be closed or can close automatically. In some embodiments, the drug preparation can be delivered into the device prior to implantation of the device.

The device and methods disclosed herein can be used for transplantation or recruitment of any therapeutically-relevant cells, or combination of cells, into a host body for providing therapeutic biological material to the host for the treatment of a disease condition. The cells may be allogeneic, xenogeneic, or syngeneic cells, or patient derived cells, including stem cells, cord blood cells, and embryonic stem cells. The stem cells may be differentiated into appropriate therapeutic cells. The cells may be immature or partially differentiated or fully differentiated mature cells when placed or recruited into the device. The cells may also be genetically engineered cells or cell lines.

In some aspects, the device can be used for transplantation of insulin producing cell aggregates (ILIPAs), Leydig cells, pancreatic islet cells, or a combination thereof.

Also disclosed are methods of treating various diseases by transplanting therapeutic amounts of cells to subjects in need thereof using the devices disclosed herein.

Other diseases and disorders which may be treated using the devices described herein include hypogonadism, hypothyroidism, rheumatoid arthritis, multiple sclerosis, and Alzheimer's disease.

In one non-limiting embodiments, methods are provided for treating cancer in a subject using the devices described herein. In such embodiments, the reservoir chamber may be primed with appropriate immune adjuvants (for example GM-CSF, CpG ODN, imiquimod) and the cell chamber may be primed with a cell lysate obtained from cells for the cancer to be treated.

In some embodiments, methods are provided for inducing an immune response against an antigen using the devices described herein. In such embodiments, the reservoir chamber is loaded with one or more appropriate immune adjuvants and the cell chamber is loaded with the antigen. The one or more immune adjuvants recruit immune cells to the cell chamber containing the antigen and assist in the induction of an immune response by said cells.

In some embodiments, methods are provided for treating an autoimmune disorder caused by an inappropriate immune response against an autoantigen using the devices described herein. In such embodiments, the reservoir chamber is loaded with the autoantigen which recruits immune cells to inhabit the protected cell chamber. The long-term, low level exposure helps to diminish over time the immune response to the autoantigen. Representative examples of disorders which could be treated by such methods include type 1 diabetes (using beta islet cell proteins and/or GAD 65 as the autoantigen), rheumatoid arthritis (using type II collagen, gp39, and/or dnajp1 as the autoantigen), or multiple sclerosis (using myelin-based proteins as the autoantigen).

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The devices, methods and compositions of the appended claims are not limited in scope by the specific devices, methods and compositions described herein, which are intended as illustrations of a few aspects of the claims, and any devices, methods and compositions that are functionally equivalent are within the scope of this disclosure. Various modifications of the devices, methods and compositions in addition to those shown and described herein are intended to fall within the scope of the appended claims. Further, while only certain representative devices, methods, compositions and aspects of these devices, methods and compositions are specifically described, other devices, methods and compositions and combinations of various features of the devices, methods and compositions are intended to fall within the scope of the appended claims, even if not specifically recited. Thus, a combination of steps, elements, components, or constituents can be explicitly mentioned herein; however, all other combinations of steps, elements, components and constituents are included, even though not explicitly stated.

Example 1. Neovascularized Implantable Cell Homing Encapsulation System with Tunable Local Drug Delivery for Allogeneic Cell Transplantation Technological advances in cell encapsulation are poised to profoundly transform the field of cell transplantation for management of chronic medical conditions, including cardiovascular, neurodegenerative, autoimmune, and endocrine disorders [1-4]. Cell encapsulation confines transplanted cells within an environment that permits effective mass transport for prolonged cell viability. For allotransplantation, encapsulation systems could prevent graft rejection by protecting from the host immune response [5]. Although various encapsulation approaches have progressed into clinical trials, results have yet to reach the degree of success necessary for clinical adoption [1, 6, 7].

The two overarching challenges in cell encapsulation approaches are host immune rejection and limited host vascular support. While physical immunoisolation using semipermeable membranes can protect encapsulated cells from the host immune system, poor oxygen permeability and lack of vascularization through the encapsulation material creates a hypoxic environment inhospitable for long-term cell viability. Efforts to address encapsulation anoxia with exogenous oxygen supplementation through external ports (β-Air; BetaO$_2$ technologies) demonstrated clinical feasibility with daily refilling, but cell function was still compromised [8, 9]. In these studies, lack of cell apposition to blood vessels may have impaired facile mass transport critical for metabolic activity, affecting graft viability and function. Further, the limited cell survival in the majority of patients in the phase I/II clinical trial of Pec-Encap with indirect device vascularization (Viacyte) highlights the importance of achieving sufficient host vascular integration [1, 6, 7]. Encapsulation technologies such as Cell Pouch (Sernova) and Pec-Direct (Viacyte) allow for direct vascularization into the device, which is anticipated to improve engraftment in clinical studies [5]. However, these approaches have the drawback of requiring chronic administration of immunosuppressive therapy, which is toxic [10-12] and is associated with a myriad of life-threatening adverse effects, opportunistic infections, and secondary malignancies [13-18]. Therefore, there is a critical need for an encapsulation strategy that addresses both host vasculature support as well as immune protection to preserve transplanted cell viability and function.

Given that key immune rejection events occur at the transplant site, confinement of immunosuppressant to the transplant site could be effective and improve therapeutic outcome. While some preclinical approaches for local immunosuppressant delivery, such as use of hydrogels, degradable polymer-based microspheres, or scaffolds, demonstrated potential [19-27], they did not address the equally critical issue of encapsulation site anoxia and ischemia.

To date, no cell encapsulation systems are available that integrate the following critical features for long-lasting cell engraftment: 1) an environment conducive to efficient mass transport (of oxygen, nutrients, therapeutic factors, etc.); 2) protection from host immune rejection via local immunosuppressant delivery; 3) biocompatibility and robust mechanical stability for long-term deployment; 4) ease of cell injection, cell replenishing, and device retrieval in the event of medical complications; and 5) scalability to achieve clinically relevant encapsulation capacity for delivery of sufficient cell mass.

Figure 1B:
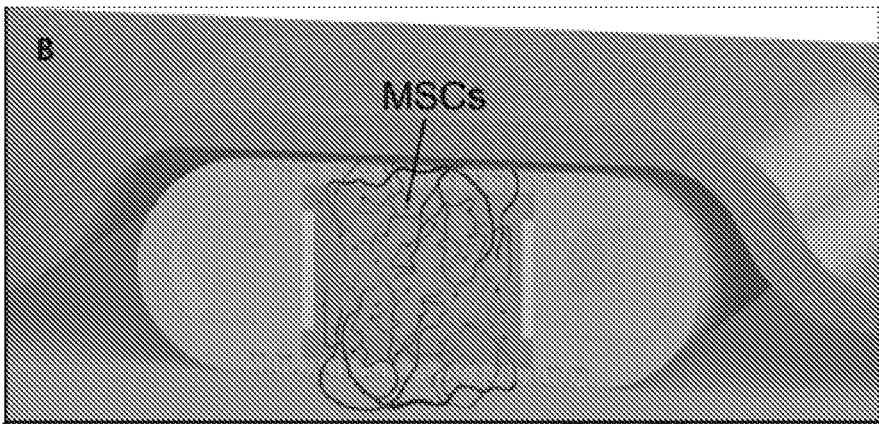
Figure 1C:
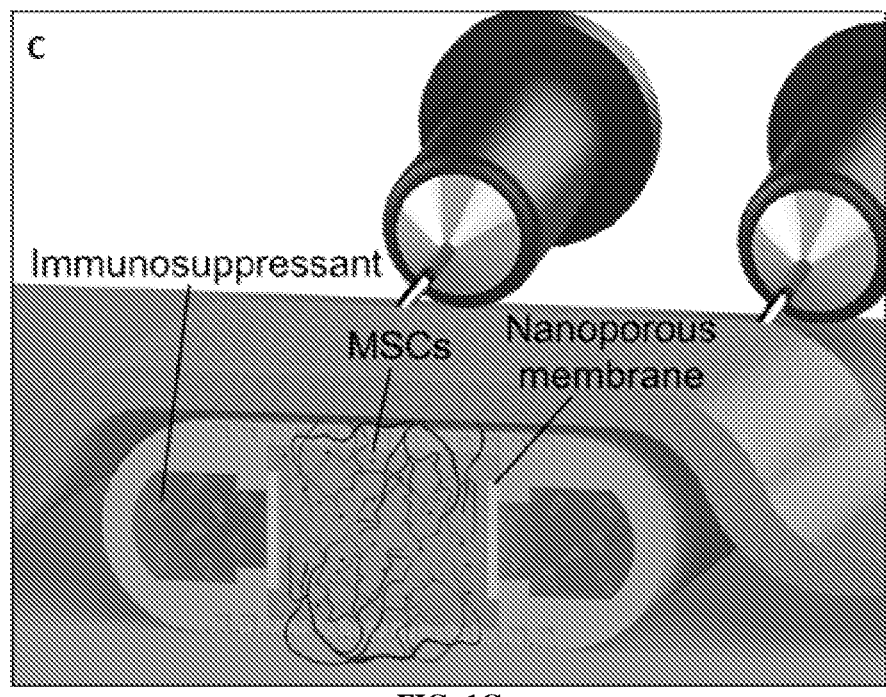
Figure 1D:
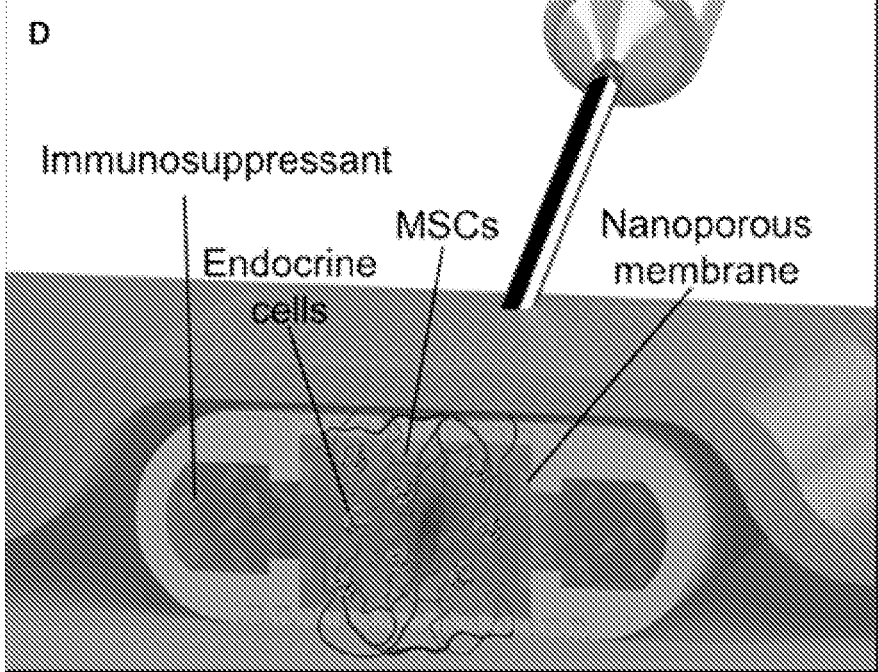

In efforts to acquire a transformative approach for cell encapsulation, we developed a cell transplantation system encompassing all the above-mentioned critical features. Our system, termed "neovascularized implantable cell homing and encapsulation" (NICHE) is a dual-reservoir encapsulation platform integrating in situ pre-vascularization and local immunosuppression. NICHE deployment first entails creating a vascularized environment. To achieve this, NICHE is preloaded with a hydrogel containing mesenchymal stem cells (MSC) and subcutaneously implanted (FIG. 1A). MSCs produce paracrine growth and angiogenic factors, which potentiate angiogenesis and tissue penetration into the cell reservoir [28, 29]. After pre-vascularization (FIG. 1B), immunosuppressant is transcutaneously loaded into the drug reservoir for local release to establish an immune-suppressed milieu (FIG. 1C). Finally, cells are transcutaneously transplanted into the cell reservoir of the preconditioned NICHE, which is a highly vascularized, immunoprotected environment conducive for engraftment (FIG. 1D).

Materials and Methods

Device Fabrication and Sterilization Procedure

NICHE was fabricated by 3-dimensional printing (Sculpteo, CA) with selective laser sintering using biocompatible polyamide PA 2200 (Electro Optical Systems). Three-dimensional datasets for the fabrication process were created using Solidworks (Dassault Systemes, Velizy-Villacoublay, France). NICHE has a flat rectangular structure and dimensions of 25 mm×14.6 mm× 5.0 mm. The drug reservoir (~345 μL) included within the main structure of NICHE has a 'U' shape and surrounds the cell reservoir (19 mm×6 mm× 4.4 mm; 502 mm$^3$) on 3 sides. Immunosuppressant drug is eluted from the drug reservoir into the cell reservoir through two 100-nm nanoporous nylon membranes (GVS, Sanford, ME), which are affixed between the drug and cell reservoirs with implantable-grade, biocompatible fast-cure silicone adhesive (MED3-4213; NuSil). The top and bottom surfaces of the cell reservoir are created by 2 nylon meshes, an inner nylon mesh with 300 μm×300 μm openings, and an outer nylon mesh with 100 μm×100 μm openings. Assembled NICHEs were sterilized with sequential washes of 0.3% H$_2$O$_2$, 0.03% H$_2$O$_2$, 70% ethanol, and sterile H$_2$O under a clean laminar flow hood.

Assessment of Polyamide PA 2200 Degradation

Three-dimensionally printed NICHEs (n=10) were weighed and completely immersed in glass scintillation vials containing 22 mL of phosphate-buffered saline (PBS; Gibco) and incubated at 37° C. At weeks 1, 2, 4, 6, 8, 16, and 32 NICHEs were dried and their weights were recorded (XPE56 Microbalance; Mettler Toledo Greifensee, 174 Switzerland). Material degradation was assessed via weight change percentage relative to day 0 using the following equation:

$$WC \% = W_t W_0 / W_0 \times 100$$

Where $W_0$ is the original device weight and $W_t$ is the device weight at each time point.

Scanning Electron Microscopy (SEM) Imaging

Nylon meshes and membranes were fixed in 10% formalin, dehydrated in ethanol and sputtered with 7 nm iridium. Imaging was performed using Nova NanoSEM 230.

In Vitro Cytotoxicity Assays

To assess the biocompatibility of NICHE and toxicity of Cytotoxic T-Lymphocyte Associated protein 4 Immunoglobulin (CTLA4Ig), we performed cytotoxicity studies on mesenchymal stem cells (MSCs), human umbilical vein endothelial cells (HUVECs), and rat Leydig cells (LC540). MSCs were cultured in StemXVivo Mesenchymal Stem Cell Expansion Media (R&D Systems); HUVECs were cultured in endothelial cell growth medium (Angio-Proteomie); Leydig cells were cultured in Eagle's minimal essential medium supplemented with 10% FBS, 100 U/mL penicillin, and 100 μg/mL streptomycin. NICHE extract was generated as follows: sterile NICHEs were incubated with 12 mL of appropriate medium for each cell line at 37° C. for 72 h. The 100% extract was then diluted to 50% and 25% using complete medium pre-incubated at 37° C. for 72h. For cell viability assays, 5×10$^3$ cells/well were seeded in 96-well plates and incubated overnight to allow cell adherence. The next day, culture medium was aspirated and replenished with 50%, or 25% extract or with complete medium containing the immunosuppressant CTLA4Ig (Orencia; Bristol-Myers-Squibb) at final concentrations of 5, 25, or 50 μg/mL. Twenty-four hours later, MTT assay was performed using the TACS MTT cell proliferation assay (R&D systems) following the manufacturer's instructions.

In Vitro CTLA4Ig Release Assays

CTLA4Ig was conjugated to Alexa Fluor 647 NHS ester (Invitrogen) following the manufacturer's instructions. Then 1, 2, 3.4, and 11 mg/mL CTLA4Ig stock solutions were made by mixing unlabeled and AlexaFluor647-conjugated drug at a 9:1 ratio. Stock solutions were injected into the drug reservoir of NICHEs (n=5/group) using 25G needles. Loaded NICHEs were submerged in glass scintillation vials containing 22 mL of PBS and incubated at 37° C. under magnetic agitation. Every third day, samples of sink solution were collected and measured with a fluorometer and the sink solution was fully replenished.

Generation of Bioluminescent Cell Line

HEK293T cells (ATCC) were used for transfection. Twenty-four hours before transfection, $5 \times 10^5$ cells were seeded on a 6-well plate. On the day of transfection, cell culture medium was replaced with 1 mL of fresh complete medium. Two 1.5-mL Eppendorf tubes were prepared. One tube contained a mixture of 1 mL of serum-free DMEM, 4 µg of pHIV-luc-ZsGreen plasmids (Addgene #39196), 3 µg of psPAX2 plasmids (for packaging, Addgene #12260), and 1 µg of pMD2.G plasmids (for expressing VSV-G, Addgene #12259). The other tube contained a mixture of 1 mL of serum-free DMEM and 21 µL of polyethyleneimine (linear, 25,000MW, ChemCruz, sc-360968, stock solution 1 mg/mL in dH$_2$O). The contents of tubes 1 and 2 were mixed in a single tube and incubated for 20 min at room temperature. The HEK293T cells were incubated with the transfection mixture overnight, and then the mixture was replaced with fresh complete medium. Twenty-four hours later, the medium containing lentivirus was filtered and used for transduction. To establish bioluminescent cell line LC540-luc-ZsGreen, 80% confluent LC540 cells (Leydig cells) were transduced with lentivirus-containing medium for 24 h. After several passages, ZsGreen-positive cells were sorted by FACS (BD FACS Aria III) and used for experiments.

Animal Models

Eight-week-old Wistar Furth rats (Charles River, Houston, TX, USA) were used in this example. All animals were maintained and used in conformity with guidelines established by the American Association for Laboratory Animal Science. Rats were kept in the Houston Methodist Research Institute animal facility, and all procedures were approved by the Houston Methodist Institutional Animal Care and Use Committee and had access to food and water ad libitum.

Generation and Implantation of MSC-NICHEs and Vascularization Study

Figure 3C:
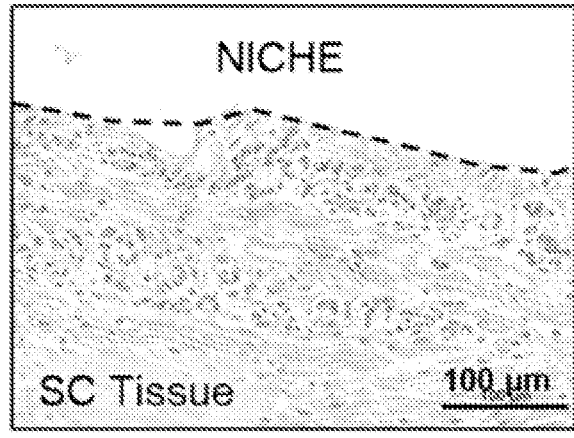

MSCs isolated from bone marrow of Wistar Furth rats were obtained from Cyagen at P2 and expanded in vitro using StemXVivo Mesenchymal Stem Cell Expansion Media (R&D Systems). Osteogenic, chondrogenic and adipogenic differentiation potential was confirmed to ensure MSC lineage (FIGS. 10A-10F). On implantation day, MSCs were suspended in a pluronic F-127 hydrogel (15% PF-127 in Expansion Media) injected into the cell reservoir of NICHEs to generate MSC-NICHEs (FIGS. 3A-C). For implantation of MSC-NICHEs, immunocompetent, 8-week-old male Wistar Furth rats were anesthetized using 2% isoflurane in 1.5. L of oxygen. Upon confirmation of absence of pedal withdrawal reflex, a subcutaneous pocket was created, and the MSC-NICHEs were aseptically implanted (1 per animal) in the right dorsum. The wound was closed using clips, and rats were allowed to recover under heat supplementation until motor skills were regained. Rats were monitored every day thereafter to confirm animal well-being.

For the vascularization study, sterile NICHEs (n=5 per group) were filled with 250,000 or 500,000 MSCs suspended in 15% PF-127 while vehicle controls were filled only with 15% PF-127. Six weeks post-implantation, rats were killed via CO$_2$ asphyxiation, NICHEs retrieved from the subcutaneous pocket, and processed for histology. For blood vessel quantification, four fields of view of each H&E-stained slides were captured at 200× magnification with an Olympus IX81 wide field microscope (Olympus, Tokyo, Japan) by an individual blinded to the treatment groups. Blood vessel counting was performed by three independent scientists blinded to the treatment groups.

Immunosuppression and Cell Transplantation

Six weeks after NICHE implantation (pre-vascularization period), rats were randomized into 3 experimental groups: no-drug control (CTRL), local (NICHE), and daily systemic (IP) immunosuppression. Rats in the control group received no treatment. Rats in the NICHE group received loading of drug reservoir with 55 mg/mL CTLA4Ig (Orencia; Bristol-Myers Squibb). Rats in the IP group received daily intraperitoneal (i.p.) injections (500 µg/day) of CTLA4Ig. Upon initiation of immunosuppression, $2 \times 10^6$ Leydig cells and $5 \times 10^5$ MSCs in a 1:1 matrigel: PBS mixture were transcutaneously loaded in the NICHE cell reservoir of all rats using a 27G needle attached to a 1-mL syringe. To assess plasma CTLA4Ig levels, blood was collected from the saphenous vein before and every 4 days after initiation of CTLA4Ig treatment in heparinized tubes and plasma was isolated via centrifugation. To assess tissue CTLA4Ig levels, NICHE, the fibrotic capsule and skin surrounding NICHE, liver, spleen, and kidneys were harvested and homogenized in T-PER buffer supplemented with protein inhibitor cocktail (Thermo Scientific). Tissue homogenates were clarified via centrifugation and stored frozen until analysis. CTLA4Ig in plasma and tissue homogenates was quantified using human CTLA4 ELISA (Invitrogen) following the manufacturer's instructions.

In Vivo Cell Tracking

Before and every 4 days after cell loading into the NICHE cell reservoir, cell viability and permanence within NICHE were assessed via bioluminescence in vivo imaging system (IVIS; Perkin Elmer). Briefly, rats received i.p. injections of 150 mg/kg D-Luciferin potassium salt solution (Gold Biotechnology). Thirty-four minutes later, anesthetized rats were imaged using bioluminescence IVIS spectrum with auto-exposure setting.

In Vivo Drug Reservoir Refillability Assessment

NICHEs implanted in rats were transcutaneously loaded with CTLA4Ig-Alexa Fluor 647 conjugate and imaged via fluorescence IVIS with excitation and emission filters of 640 nm and 680 nm, respectively. Background threshold was obtained by acquiring an image of implanted empty NICHE prior to CTLA4Ig-Alexa Fluor 647 loading.

Histology Analysis and Blood Vessel Quantification

Upon harvesting, tissues were rinsed with PBS and fixed in 10% formalin for 48 h. Fixed tissues were sequentially incubated in 15% and 30% sucrose/PBS for 24 h followed by embedding in optimal cutting temperature medium (OCT) for generation of frozen sections. Alternatively, fixed tissues were dehydrated and cleared using standard ethanol and xylene washes followed by embedding with paraffin or Poly(methyl methacrylate) (PMMA) resin. 5-µm sections were cut and stained with hematoxylin-eosin or Masson's Trichrome and visualized using an Olympus IX81 wide field microscope (Olympus). For immunofluorescence staining, 5 μm sections were blocked in 5% normal goat serum for 1 h at room temperature. Primary antibodies were incubated for 16 h at 4C in renaissance antibody diluent (Biocare Medical, California, USA) and secondary antibodies for 1 h at room temperature in blocking buffer. Mounting media with DAPI was added to preserve fluorescence (Invitrogen). Sections were visualized using a FluoView™ 3000 confocal microscope (Olympus). Antibodies used were: alpha smooth muscle actin (a-SMA; ab56894, Abcam), RECA-1 (sc-52665, Santa Cruz), Firefly luciferase (35-6700, Invitrogen) CD3 (MA1-90582, Invitrogen), AlexaFluor 488 goat anti-rabbit (ab150077, Abcam), AlexaFluor 647 goat anti-mouse (ab150115, Abcam), AlexaFluor 488 goat ant-mouse (ab150113, Abcam), AlexaFluor 555 goat anti-rabbit (A21428, Invitrogen).

Statistical Analysis

Results are expressed as mean±standard deviation. Statistical analyses were performed using Prism 8 software (GraphPad Software Inc., San Diego, CA, USA). One-way analysis of variance was performed to determine statistical significance of differences among groups, and P values less than 0.05 were considered significant. Significance was indicated as follows: n.s., not significant; *, $p < 0.05$; , $p \leq 0.01$; and *, $p \leq 0.001$.

Results

NICHE Fabrication and Loading

To integrate both in situ prevascularization and local immune-suppressant delivery into an encapsulation platform, NICHE was developed as a dual reservoir system. A central cell reservoir is surrounded by a 'U'-shaped drug reservoir that sustainably elutes immunosuppressant through two nanoporous nylon membranes (FIG. 2, Panel A). The drug reservoir, which serves as the backbone of the NICHE, is fabricated using selective laser sintering (SLS) in biocompatible nylon (PA 2200). Additive manufacturing permits rapid scalability and flexibility for device size and geometry customization. The drug reservoir has two longitudinal 2.3 mm×15 mm rectangular windows (FIG. 2, Panel A) on either sides of the cell reservoir. Two nanoporous nylon membranes are affixed onto the rectangular windows using biocompatible silicone glue (FIG. 2, Panel B). Two biocompatible silicone plugs on the 'U'-shaped drug reservoir serve as the loading and venting ports for transcutaneous drug replenishment. A two-layered woven nylon mesh system encloses the cell reservoir (FIG. 2, Panel D): an inner 300 μm×300 μm nylon mesh provides mechanical support, while an outer 100 μm×100 μm nylon mesh allows for blood vessel penetration and cell retention [30]. Importantly, SEM imaging of woven meshes and nanoporous membranes obtained from NICHE after implantation in rats for 10 weeks showed material integrity remained intact (FIG. 2, Panels B-E). We observed extensive tissue colonization of the woven mesh openings after implantation, which further contributes to cell retention in NICHE (FIG. 2, Panel E).

While the NICHE can be implanted anywhere in the body, including the omentum, we focus on subcutaneous implantation, which facilitates straightforward and minimally invasive transcutaneous loading of cells and drug into the respective reservoirs. Loading of the drug reservoir is achieved by advancing needles through the skin and the silicon ports. One needle serves for drug loading, while the other vents out air or excess drug solution. The architecture avoids any chance of nanoporous membrane puncture. Cell loading is performed by advancing a needle parallel to the skin, through the nylon meshes, and into the cell reservoir. Finally, the internal wall of the cell reservoir serves as a backstop and landmark, guaranteeing cells are being dispersed within the cell reservoir.

Polyamide PA 2200 Degradation and Biocompatibility

As NICHE is intended for long-term deployment, we sought to investigate material stability in vitro. To this end, we assessed polyamide PA 2200 (the material of which NICHE is constructed) degradation in vitro at 37° C. in PBS through specimen weight change. We observed a 0.5% increase in the weight of the device at 1 week of incubation (FIG. 3A). The weight continued to steadily rise at a rate of 0.1% per week for up to 8 weeks. Thereafter, up to a total 1.5% weight increase was detected at 32 weeks (0.01% per week). We attribute this weight increase to water absorption by the material, in line with literature reports for this type of material [31, 32].

Figure 3D:
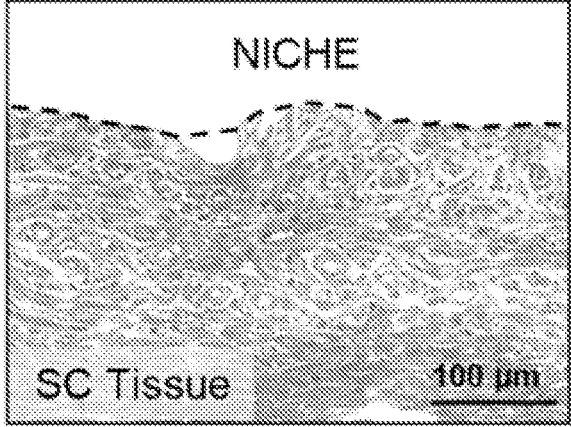
Figure 3E:
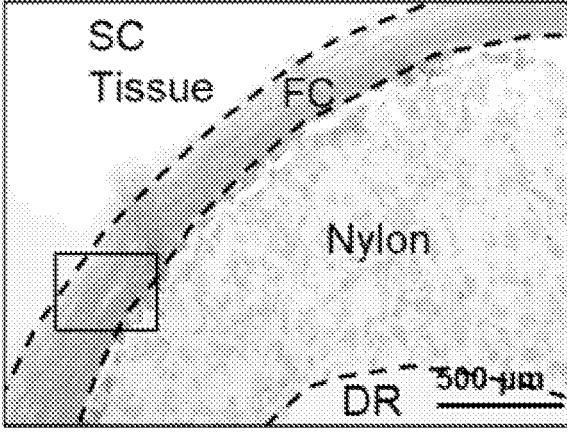
Figure 3F:
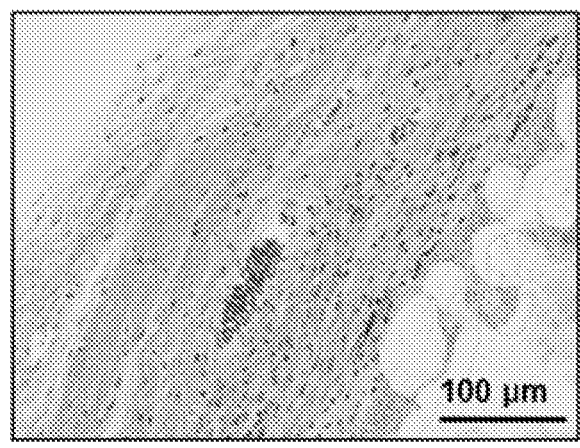

To assess biocompatibility of NICHE, we performed cytotoxicity studies with representative cell lines relevant to our deployment strategy as well as through in vivo implantation in rats. Cytotoxicity of NICHE was evaluated via MTT cell viability assay in Leydig cells, Mesenchymal Stem Cells (MSC) and Human Umbilical Vein Endothelial Cells (HUVECs) as representatives of model endocrine cells for transplantation, stem cells for local angiogenesis and immune modulation, and endothelial cells involved in the formation of the vascular network, respectively. In comparison to media only (Veh), cells incubated in NICHE extract maintained viability well above the 70% threshold in accordance to ISO standard 10933-5 (FIG. 3B). This indicates that NICHE does not have a toxic effect on mammalian cells. To further characterize the biocompatibility of NICHE, we performed an in vivo implantation test in the subcutaneous tissue of rats. Histological evaluation of subcutaneous tissue in direct contact with NICHE collected after a ten-week implantation period showed a marginal foreign body reaction characterized by granulation tissue with neovessel formation and without chronic inflammation, exacerbated fibrosis, giant cell or mast cell infiltration (FIGS. 3C-D). Typical of medical device implantation, a fibrotic capsule formed around NICHE at the interphase between the polymer and the subcutaneous (SC) tissue (FIG. 3E). The capsule was thin (313.28+84.49 μm) and infiltrated with large, non-inflamed vessels, suggesting limited reactivity to the implant (FIG. 3F). It is noteworthy that the thickness of the fibrotic capsule was comparable to that reported by other medical devices implanted for similar time periods [33, 34]. Taken together, these results indicate NICHE was mechanically stable and biocompatible.

In Vivo NICHE Vascularization

Figure 4A:
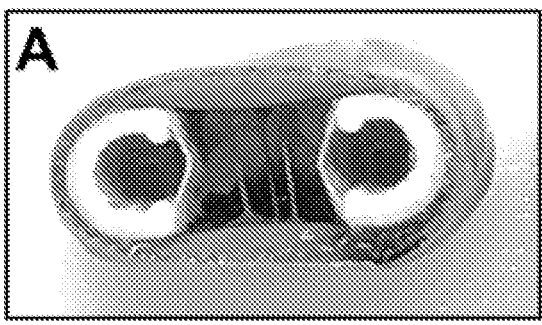
FIGS. 4A-4L depicts NICHE pre-vascularization using MSC. Gross cross-sections of explanted NICHE from rats after a 6-week pre-vascularization period using (FIG. 4A) vehicle hydrogel (CTRL) or hydrogel containing (FIG. 4B)
Figure 4B:
Figure 4C:
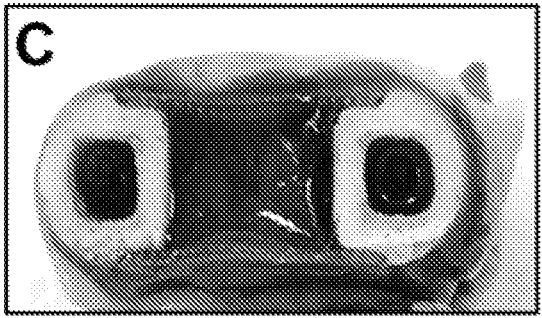
Figure 4D:
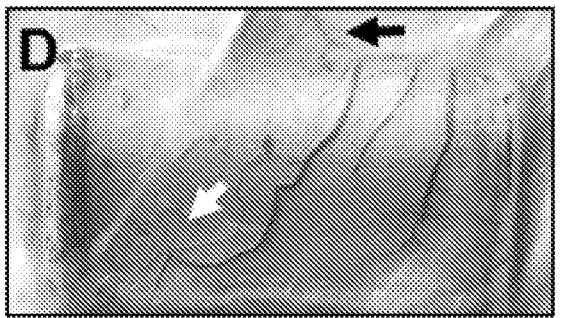
Figures 4E, 4F, 4G, 4H, 4I, 4J:
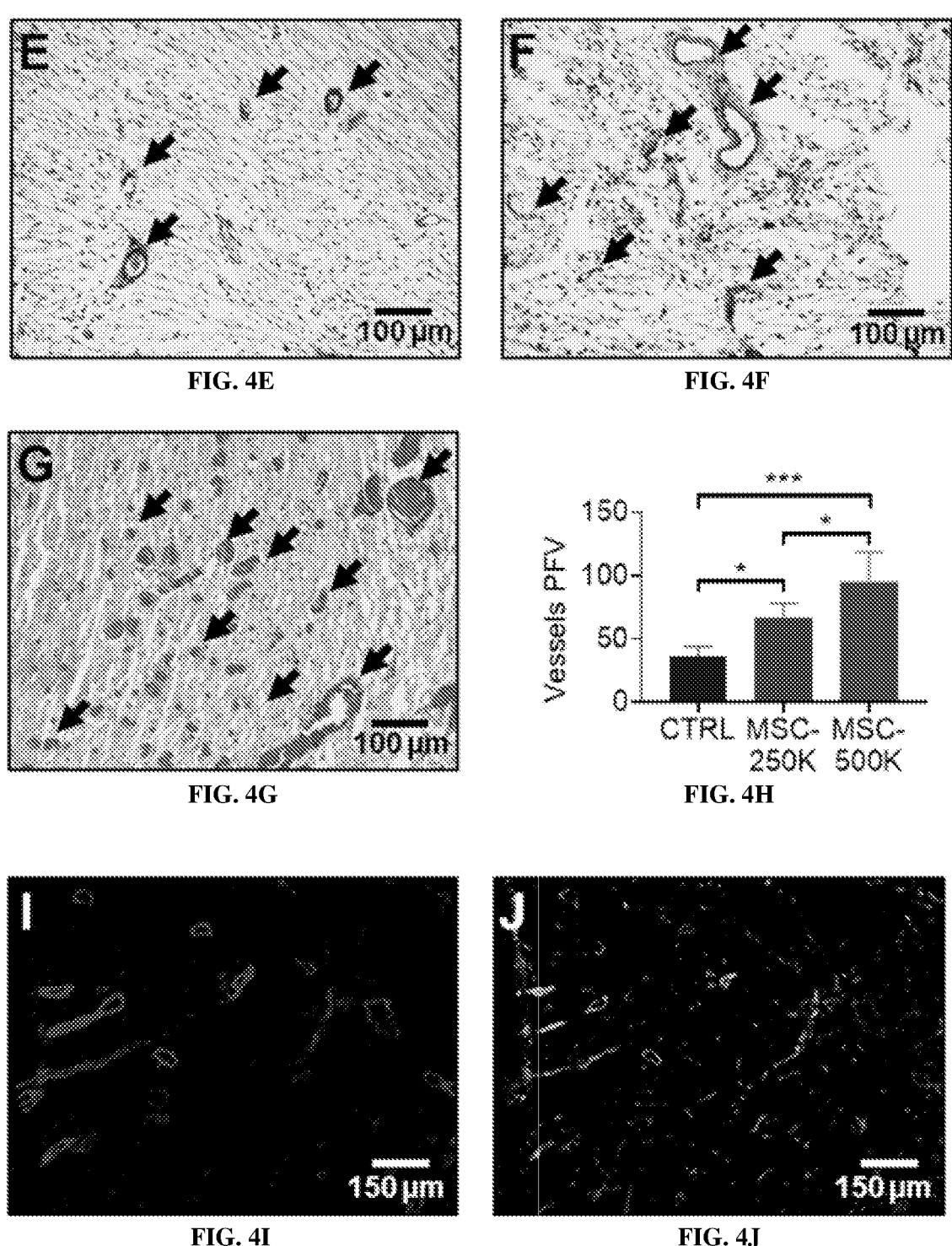
Figures 4K, 4L, 5A, 5B, 5C, 5D:
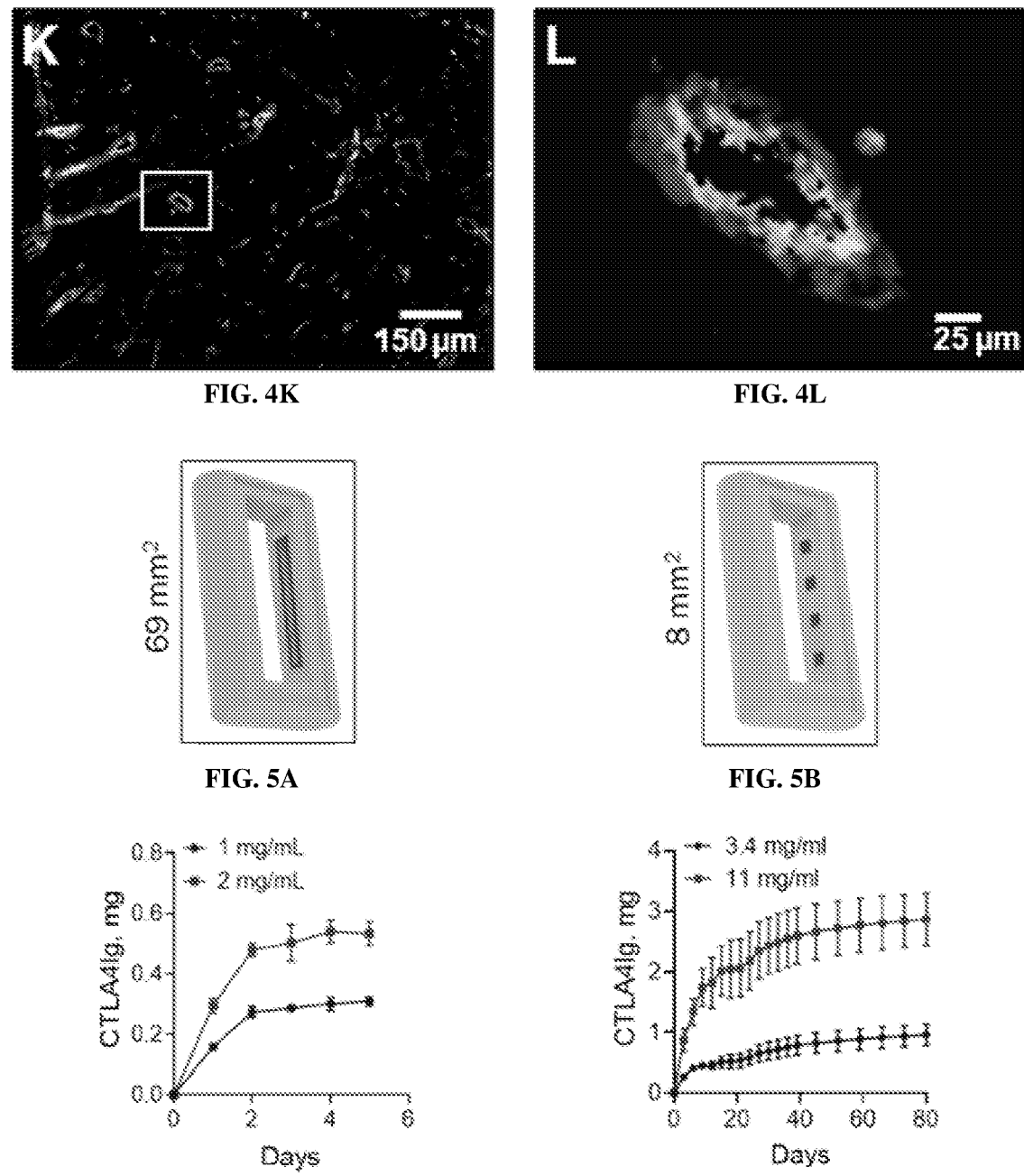
FIGS. 5A-5G depicts CTLA4Ig in vitro release and cytotoxicity. 3D rendering of NICHE with (FIG. 5A) 69 mm$^2$ and (FIG. 5B) 8 mm$^2$ drug reservoir surface exchange areas delineated in blue. In vitro CTLA4Ig release from NICHE with (FIG. 5C) 69 mm$^2$ or (FIG. 5D and FIG. 5E) 8 mm$^2$ surface exchange areas.
Figures 7E, 7F, 8A, 8B, 8C:
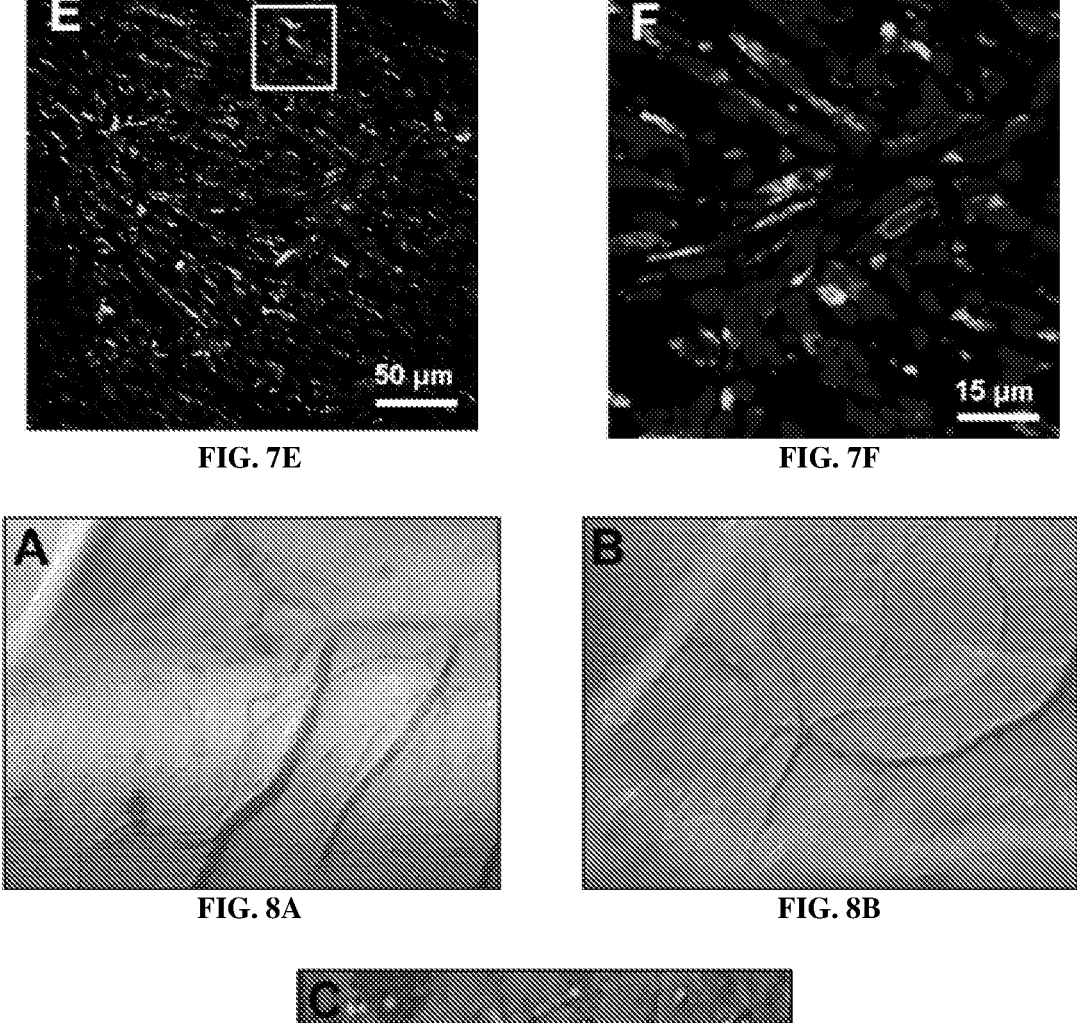
FIGS. 8A-8C depicts optical images of NICHE incorporated in the subcutaneous tissue of rats 6 weeks post implantation with visible blood vessels (FIG. 8A) branching from the subcutaneous tissue and (FIG. 8B) penetration into the cell reservoir.
Figure 9A:
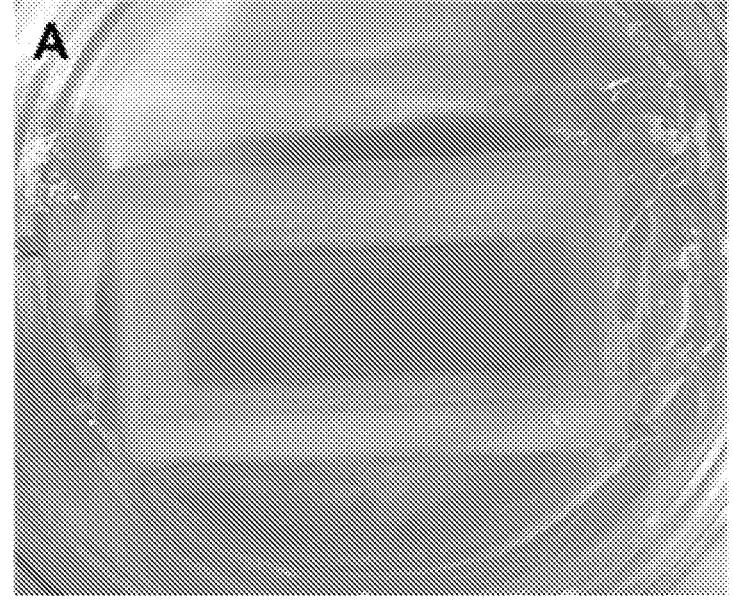
FIGS. 9A-9C depicts (FIG. 9A) optical image of NICHE filled with NSC-hydrogel prior to implantation and fluorescent imaging of Dil-labeled MSCs inside NICHE cell reservoir (FIG. 9B) prior to implantation and (FIG. 9C) 6 weeks post-implantation (red).
Figure 9B:
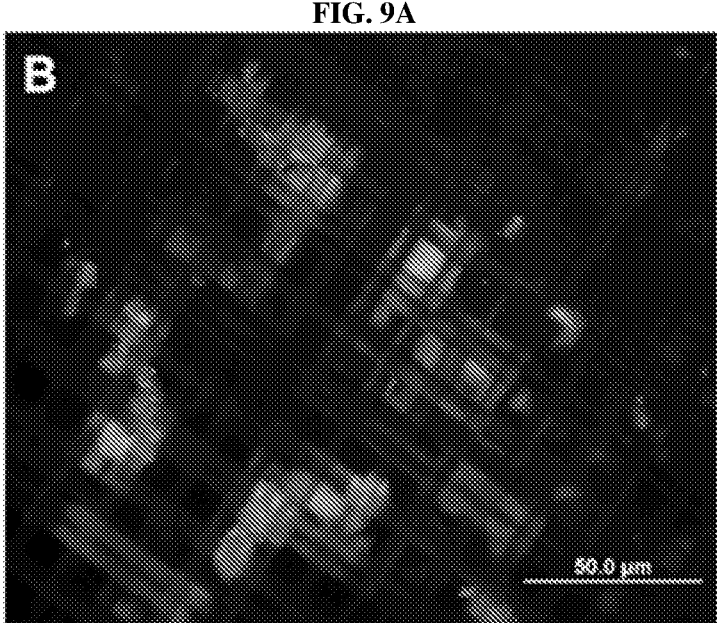
Figure 9C:
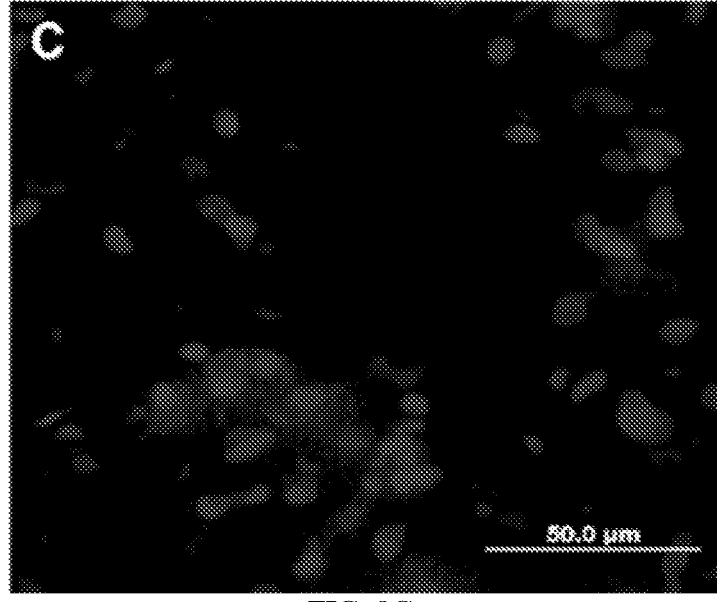
Figure 10A:
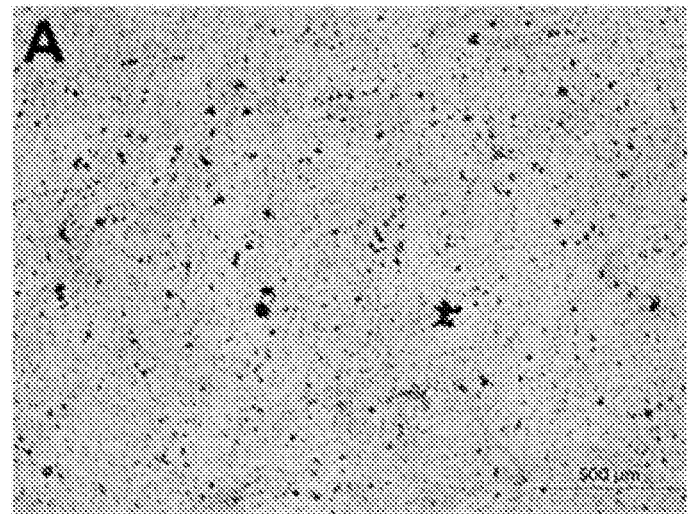
FIGS. 10A-10F depicts images of MSC after (FIG. 10A and FIG. 10B) osteogenic, (FIG. 10C and FIG. 10D) adipogenic, and (FIG. 10E and FIG. 10F) chondrogenic differentiation.
Figure 10B:
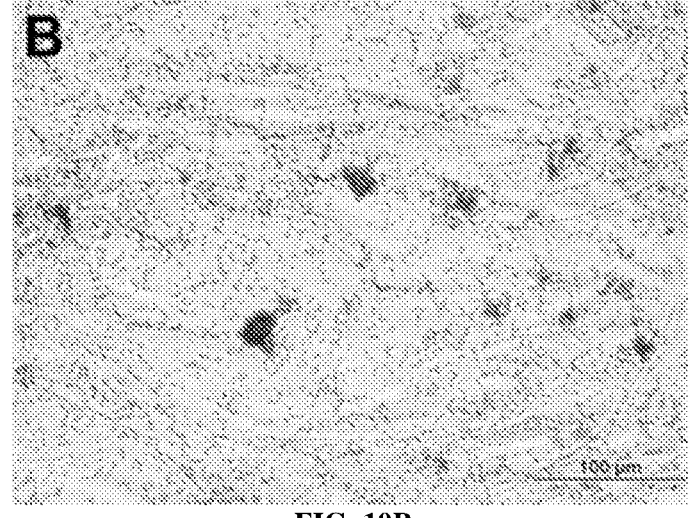
Figure 10C:
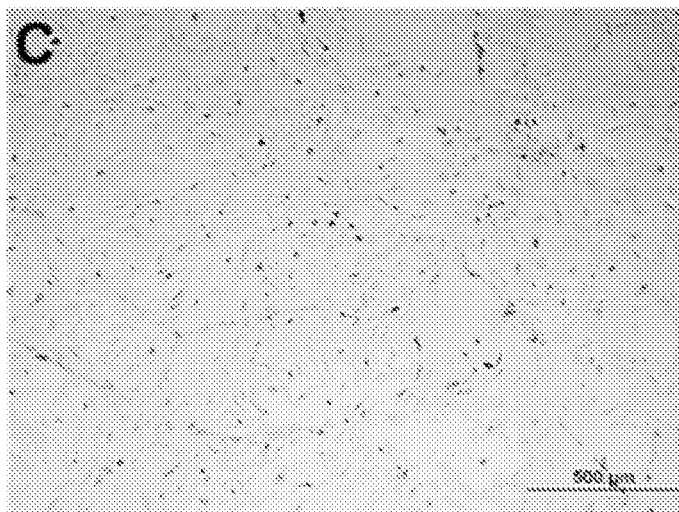
Figure 10D:
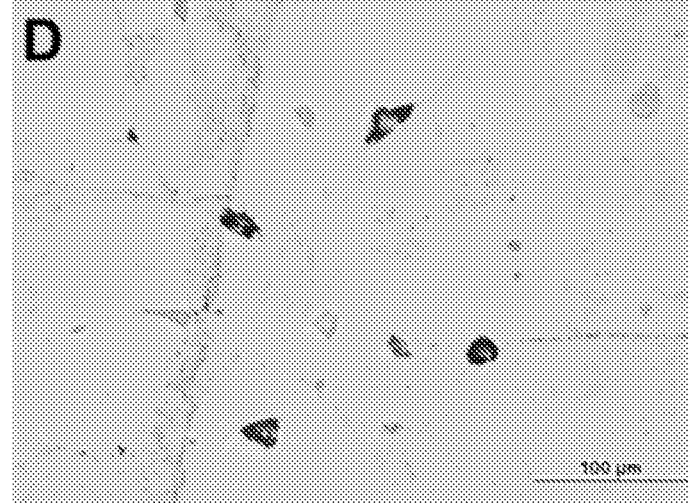
Figure 10E:
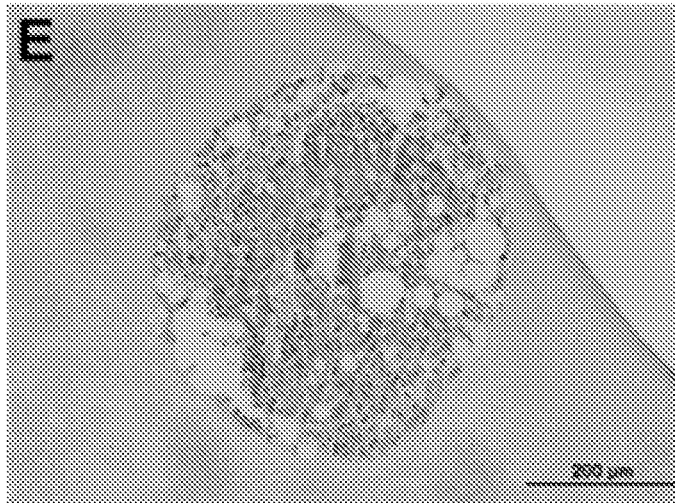
Figure 10F:
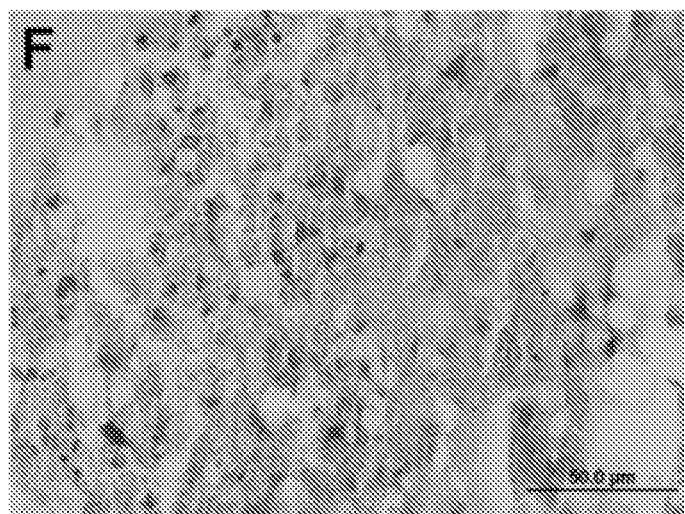

As oxygen and nutrient delivery to transplanted cells is imperative for engraftment and survival, we sought to create a highly vascularized environment that would provide adequate mass transport to and from the graft. To this end, we explored the use of MSCs for their known abilities to drive vascularization [35]. We subcutaneously implanted NICHEs filled with vehicle hydrogel as control (FIG. 4A), and either 250,000 (FIG. 4B) or 500,000 MSCs (FIG. 4C) in rats and allowed for a vascularization period of 6 weeks. Upon explantation, NICHE was bio-integrated into the subcutaneous tissue with visible blood vessels branching from the host tissue, through the nylon meshes, and penetrating into the device (FIG. 4D and FIGS. 8A-B). Gross analysis of cross-sections of NICHEs revealed implantation with MSCs increased tissue penetration into the cell reservoir (FIGS. 4A-C) with macroscopic vessels scattered throughout (FIG. 8C). With respect to vehicle control (FIG. 4E), histological examination showed increased patent, red blood cell-laden vessels embedded in a collagenous extracellular matrix in MSC-loaded NICHE (FIG. 3F-G). Incorporation of MSC into NICHE increased blood vessel density (vessel number per field of view) in a dose-dependent manner, with NICHEs containing 250,000 or 500,000 MSC having 1.8 (67+12) and 2.7 (96+23) times the vessel density than vehicle hydrogel (36±8), respectively (FIG. 4H). Moreover, the vascular structures within NICHE showed positive labeling for vessel markers alpha smooth muscle actin (aSMA; FIG. 4I) and rat endothelial cell antigen 1 (RECA-1; FIG. 4J). The merged immunofluorescence image of aSMA and RECA-1 showed concentric labeling with the endothelial layer surrounded by the muscularis layer, indicating vessel maturity (FIGS. 4K-L). Importantly, blood vessel markers stained positively in control as well as MSC-loaded NICHE, indicating that NICHE structure is conducive to functional and mature vessel colonization. Based on significantly higher extent of vascularization, 500,000 MSC were used for pre-vascularization of the cell reservoir in all future studies.

CTLA4Ig In Vitro Release and Cytotoxicity and In Vivo Loading

Figure 5E:
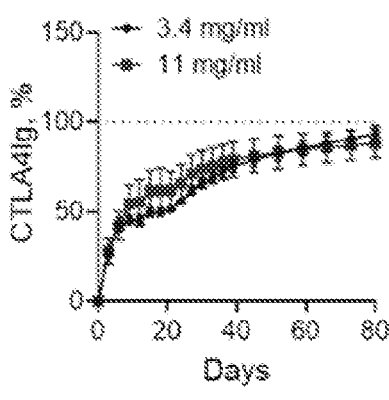
Figure 5F:
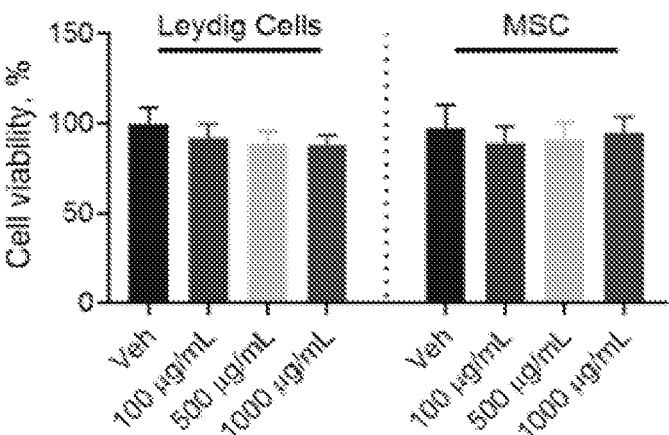

While vascularization of the cell reservoir is critical for cell viability, vasculature permits cellular influx, rendering allotransplanted cells unprotected from immune cell recognition and destruction. To overcome this issue, we incorporated a drug reservoir in NICHE for controlled delivery of immunosuppressant locally through a nanoporous membrane. We performed in vitro release assays to characterize the release profile of CTLA4Ig, an immunosuppressant with promise in preventing transplant rejection, from NICHE. One way of tuning NICHE drug release is through modification of the porous membrane surface area (FIGS. 5A-B), which elutes CTLA4Ig into the cell reservoir. As a first approach, we assessed the release across a surface area of 69 mm$^2$ (FIG. 5A) and observed a rapid release rate that plateaued by day three, independently of the drug concentration loaded (FIG. 5C). To prolong dosing, we decreased the membrane surface area to 8 mm$^2$ (FIG. 5B), which slowed CTLA4Ig release rate and revealed a biphasic release profile (FIG. 5D). During the first 10 days, devices loaded with 3.4 and 11 mg/ml released an average of 16 and 70 μg/day of drug, respectively. By day 13, the release rate decreased to 9 and 22 μg/day and remained quasi-constant for an additional 30 days. Overall, the daily release rate changed proportionally to the concentration of drug loaded, while a biphasic release profile occurred across concentrations (FIG. 5E). We demonstrated that drug delivery is tunable through altering loaded drug concentration or modifying NICHE surface exchange area. For prolonged and sustained drug dosing during transplantation, we used the 8 mm$^2$ configuration of the drug reservoir for the next in vivo experiments.

In situ immunosuppressant elution into the cell reservoir results in direct drug exposure to transplanted graft. As such, we investigated the cytotoxic effect of CTLA4Ig on Leydig cells and MSC via MTT assay. In vitro cytotoxicity studies revealed that incubation with CTLA4Ig at increasing concentrations of 100, 500, and 1000 μg/mL did not impact Leydig cell or MSC viability, with respect to media only control (FIG. 4F). This data suggests that CTLA4Ig is suitable for use in a local setting without detrimental effects on cells.

Long term deployment of NICHE would require periodic replenishment of the drug reservoir. As such, we evaluated in vivo transcutaneous refillability in rats using CTLA4Ig fluorescently labeled with Alexa Fluor 647 (CTLA4Ig-AF647), which allowed visualization of the drug via IVIS.

Figure 5G:
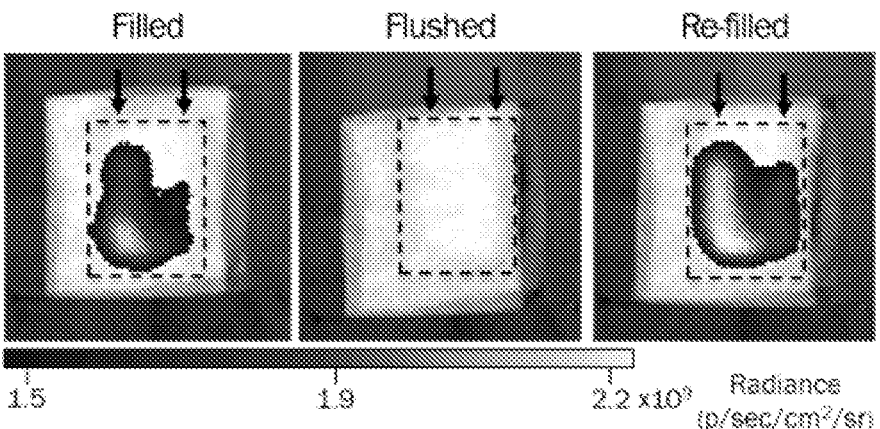

NICHE drug reservoir was transcutaneously filled with CTLA4Ig-AF647 after subcutaneous implantation (FIG. 5G). The signal intensity localized within the filled drug reservoir disappeared upon reservoir flushing with saline and was re-established once the reservoir was replenished, indicating successful transcutaneous manipulation and refilling of drug reservoir (FIG. 5G). Taken together, this data indicates that local release of immunosuppressant via NICHE is tunable, CTLA4Ig is non-toxic, and the drug reservoir is easily replenishable.

In Vivo Validation of NICHE

Figures 6A, 6B, 6C, 6D, 6E:
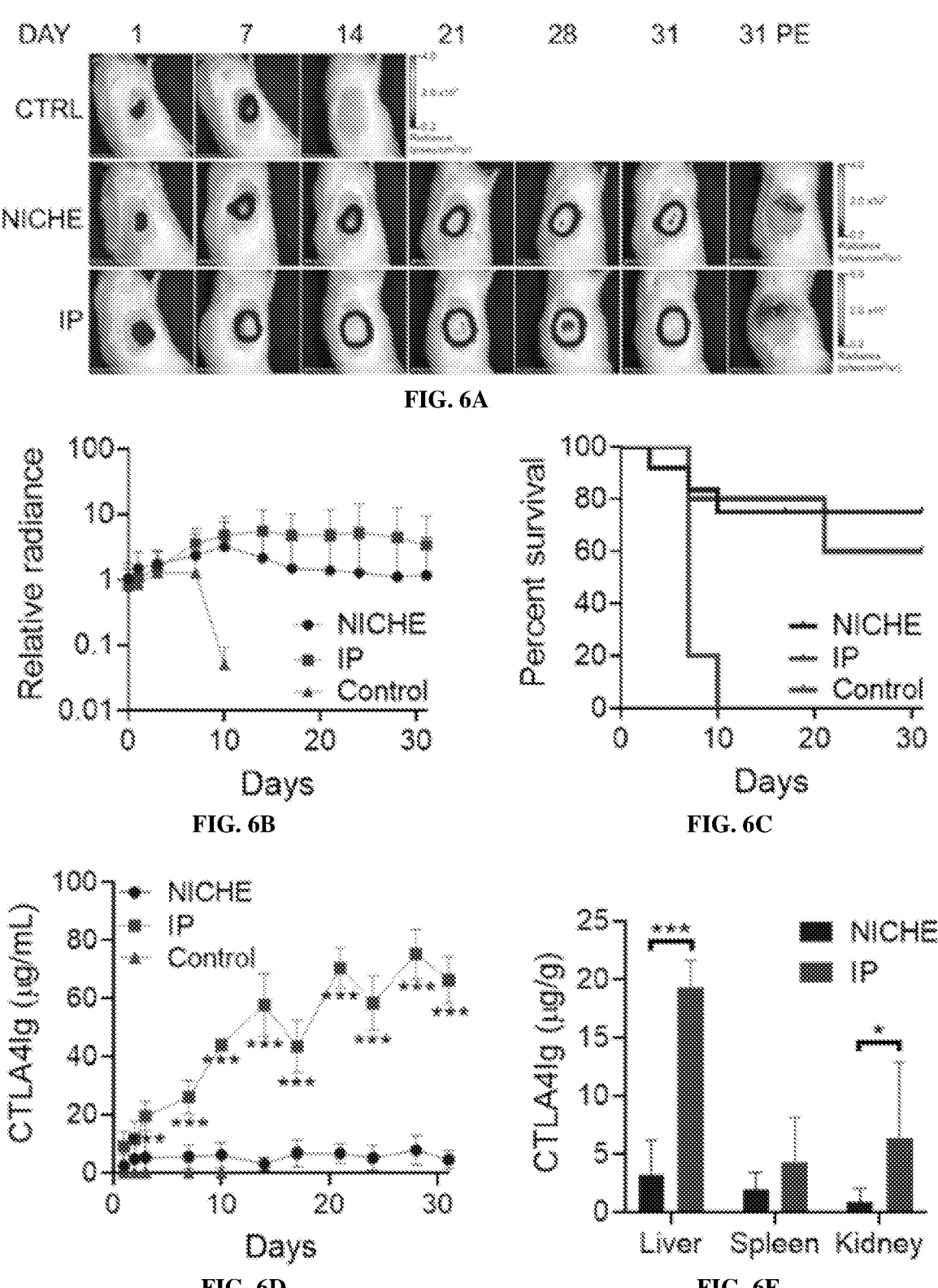
FIGS. 6A-6G depicts a NICHE efficacy study.

To assess the efficacy of our encapsulation system in vivo, we performed allogeneic Leydig cell transplantation in NICHE using immunocompetent rats following the deployment strategy described in FIGS. 1A-1D. We used luciferase-expressing Leydig cells, which allowed us to track cell viability and retention in NICHE. We compared NICHE (local CTLA4Ig immunosuppression) to daily systemic CTLA4Ig administration via intraperitoneal injection (IP), and control (CTRL) no immunosuppression. NICHE filled with 500,000 MSC were subcutaneously implanted in the dorsum of rats and allowed 6-weeks for prevascularization period. Following this, CTLA4Ig was transcutaneously loaded into the drug reservoir. Leydig cells were co-transplanted with MSC, leveraging their immunomodulatory properties that hold promise in promoting transplant engraftment and survival [28, 35]. NICHE were assessed via IVIS imaging one day after transplantation, and weekly thereafter. On day 1, all NICHEs were observed to have luminescence signal, indicative of successful cell loading and viability (FIG. 6A). By day 14 post-transplant, 100 percent of rats in the control group without immunosuppression had lost signal, whereas rats in NICHE and IP groups maintained 75% and 60% graft survival with comparable signal intensities up to day 31, indicating that immunosuppression was imperative for allogeneic cell survival (FIGS. 6A-C). Importantly, upon explantation of NICHEs at study termination on day 31, there was no residual luminescence signal, indicating that the bioluminescent cells were fully retained within NICHE (FIG. 6A, Day 31 PE).

Figures 6F, 6G, 7A, 7B, 7C, 7D:
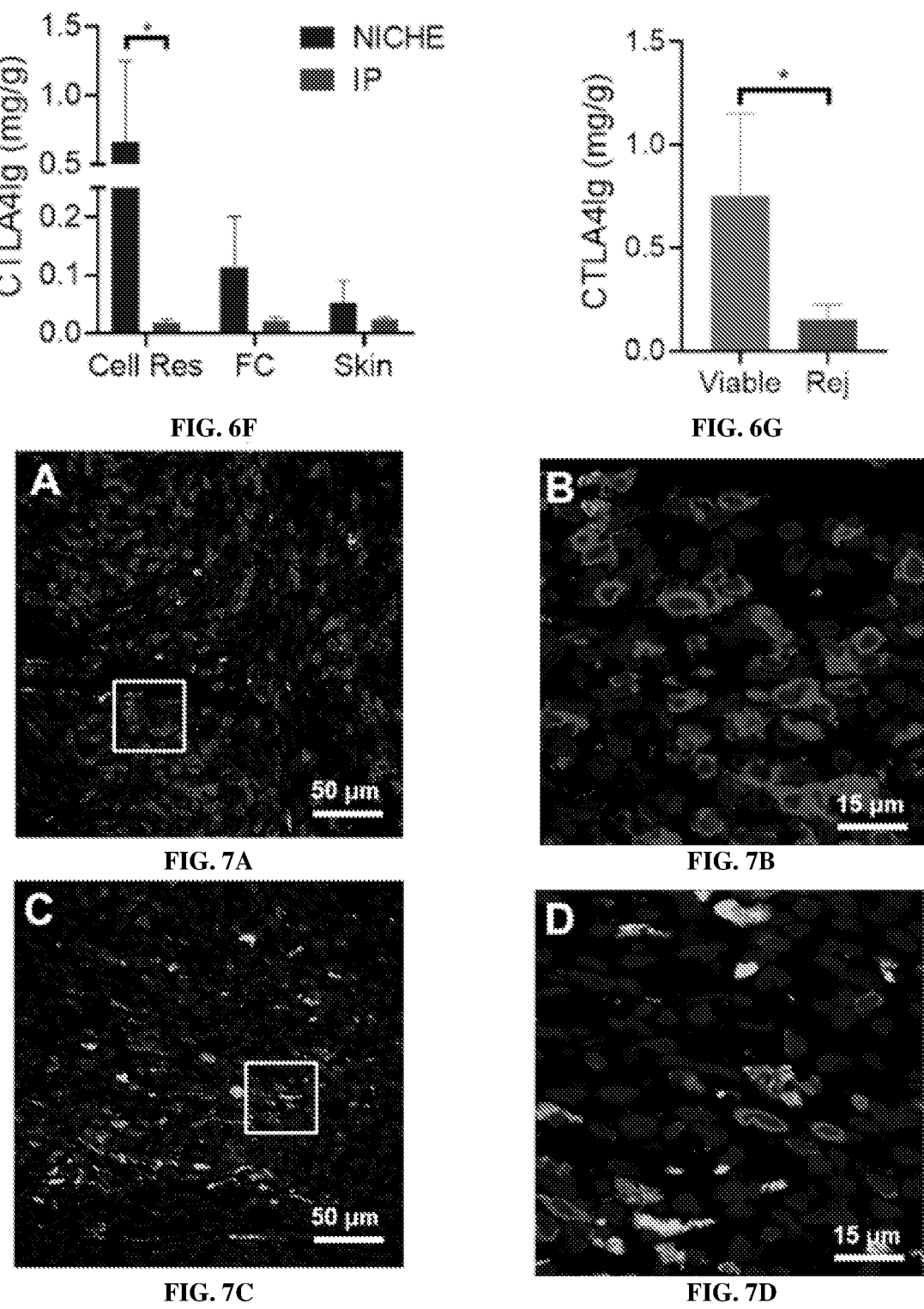
FIGS. 7A-7F depicts immunofluorescence staining of transplanted Leydig cells in NICHE. Immunofluorescence analysis of tissue collected from cell reservoirs of NICHE transplanted with Leydig cells. Sections were immunostained for DAPI (blue), luciferase/Leydig cells (green), and pan-lymphocyte marker CD3 (red). White squares indicate areas of magnification.

Exposure to immunosuppression was assessed via quantification of CTLA4Ig levels in plasma (FIG. 6D) and peripheral tissues (FIG. 6E). Rats in the control group had no detectable CTLA4Ig throughout the study. In plasma, drug levels were detectable by day 1 of administration with both NICHE (2.19±4.10 μg/mL) and IP (9.15±5.11 μg/mL) delivery. CTLA4Ig plasma concentration in the IP group escalated consistently for 14 days up to 57.67±10.79 μg/mL and fluctuated thereafter, peaking at 75.30±8.52 μg/mL on day 28. In contrast, CTLA4Ig plasma concentrations in rats receiving local immunosuppression with NICHE reached about 6 μg/mL 2 days after reservoir loading and remained stable for 10 days (FIG. 6D). On day 14, plasma concentrations dropped to ~2 μg/mL, suggesting a decrease of CTLA4Ig in the drug reservoir. At this point, the drug reservoir was transcutaneously re-loaded, which restored plasma CTLA4Ig levels to steady state. Preemptive re-filling of the drug reservoir on day 24 (10 days after first re-filling) maintained plasma levels constant throughout the remainder of the study, underscoring efficient transcutaneous refilling. Overall, systemic drug exposure was up to 12 times higher in the IP cohort, compared to NICHE. Similar to plasma, CTLA4Ig accumulation in peripheral tissues was higher in IP than NICHE group with 6-fold, 3-fold and almost 2-fold higher levels in liver, kidney, and spleen, respectively (FIG. 6E). Quantification of CTLA4Ig in the transplant microenvironment revealed that rats receiving local immunosuppression resulted in a gradient-like distribution with uppermost concentrations in the cell reservoir (0.66±0.58 mg/g), followed by the fibrotic capsule (0.11±0.08 mg/g) and skin (0.05±0.03 mg/g) (FIG. 6F). In contrast, rats receiving systemic immunosuppression had lower concentrations (~0.02 mg/g) and homogeneously low distribution of CTLA4Ig across tissues in the transplant microenvironment (FIG. 6F). Moreover, in rats receiving local immunosuppression, CTLA4Ig concentration was higher in cell reservoir tissues with viable (0.75 mg/g±0.15 mg/g) versus rejected (0.15±0.07 mg/g) grafts (FIG. 6G).

We evaluated the tissue collected from the cell reservoir of NICHE for assessment of Leydig cell engraftment and immune infiltration via histological analysis. The rejected grafts had visibly fewer engrafted cells (FIGS. 7A-B), in line with decreased IVIS signal intensity. Histological analysis of viable grafts showed Leydig cell engraftment in both local (FIGS. 7C-D) and systemic immunosuppression cohorts (FIGS. 7E-F). Moreover, CD3 (pan-lymphocyte) staining revealed increased infiltration of immune cells in rejected grafts (FIGS. 7A-B), compared to viable grafts (FIGS. 7C-F). Interestingly, in rats receiving local immunosuppression, cell reservoirs with viable grafts had higher CTLA4Ig concentrations and lower lymphocyte infiltration than those with rejected grafts, underscoring efficient local immunosuppression.

Taken together, these data suggests that NICHE microenvironment was conducive for cell engraftment and that local delivery of immunosuppressant was effective in maintaining graft viability while reducing systemic exposure up to 12-fold.

Discussion

In this example, we developed NICHE, an encapsulation platform integrating in situ pre-vascularization and local immunosuppressant delivery for engraftment of allotransplanted cells. NICHE was carefully designed to meet key components for successful cell encapsulation: biocompatibility, mechanical stability, scalability, feasibility of clinical use, efficient mass transport, and immune system evasion.

3D printing for manufacturing of medical devices in the context of tissue regeneration is widely used as it allows creation of complex designs that provide a personalized approach to meet patient need. Using selective laser sintering to manufacture NICHE provided ease of design modification and fast, cost-effective scalability. These characteristics are especially relevant for clinical translation to allow size and geometry customization depending on transplant type or individual need, and to produce enough devices to meet clinical need. Among the wide range of materials compatible with SLS, we chose nylon as it is a non-biodegradable and robust material with long-lasting tensile strength and high elasticity [32]. These characteristics make nylon an ideal material for long-term deployment inside the body by having the mechanical stability required for implantation in the subcutaneous space, where movement and exposure to external forces could compromise device integrity [36]. Further, nylon is an ideal polymer for SLS manufacturing [37], its biomedical use has been widely characterized and is readily commercially available, which allows for straightforward, reproducible elaboration of the device. Moreover, nylon is highly biocompatible and is widely used as an implantable material for various applications ranging from suture material and catheters in the clinical setting to scaffolding and cell encapsulation in pre-clinical research [36, 40]. Indeed, the results of this study showed the nylon used to construct NICHE was mechanically stable and highly biocompatible in vitro and in vivo.

Deployment of NICHE in the subcutaneous space allows straightforward, clinically relevant use in terms of ease of implantation, refillability, and retrievability. Specifically, NICHE implantation into a subcutaneous pocket required only an ambulatory and minimally invasive surgical procedure, similar to those performed currently for implantation of other subcutaneous medical devices [41]. Device placement directly under the skin renders NICHE drug and cell reservoirs easily accessible, allowing for straightforward transcutaneous filling with immunosuppressant or replenishment of cells as needed. These procedures could be easily performed in a doctor's office in an outpatient setting. Further, we demonstrated successful and minimally invasive en bloc removal of intact NICHE surrounded by a thin fibrotic capsule and with complete containment of transplanted cells, which further informed on key safety aspects should retrieval be needed due to adverse side effects.

Pre-vascularization of the transplant site has shown promise in being conducive for efficient mass transport between graft and host by reducing the distance between the transplant and source of oxygen and nutrients [42, 43]. In the context of tissue engineering, many strategies have been used to drive vascularization, including release of angiogenic factors [44], formation of scaffolds for endothelial colonization [45, 46], and co-transplantation with endothelial cells or MSCs [47, 48]. With NICHE, we used MSCs to drive vascularization into the cell reservoir by leveraging on their ability to produce an angiogenic wound healing response, serve as pericytes to promote neovessel maintenance [49], and immunomodulate their microenvironment to ameliorate immune response. Indeed, NICHEs implanted with MSCs inside the cell reservoir were significantly more vascularized than controls in a dose-dependent manner. Moreover, the vessels had well-formed endothelial and muscularis layers, indicating they were structurally mature and permanent. Additionally, successful in vivo cell tracking of the luciferase-expressing cells used in our efficacy study further informed on the maturity of the vascular network formed within NICHE and its direct connection to the systemic vasculature. For our study, rats were administered an intraperitoneal (systemic) injection of luciferin prior to imaging. Obtaining bioluminescent signal from cells within NICHE post-systemic luciferin administration requires luciferin transport to the transplant site via the systemic circulation through vasculature. Signal generation from cells within NICHE indicated that they were viable and had preserved their metabolic activity, suggesting adequate vascular perfusion. Even though the degree of vascularization achieved with our approach was sufficient to maintain cell viability in the context of our study, transplantation of other cell types may require more extensive vascularization depending on their sensitivity to hypoxia. For instance, pancreatic islets have a high oxygen demand and require extensive apposition to vascularization to develop intra-islet capillary networks [50]. In this context, NICHE versatile design could be easily adapted and coupled with one or more of the aforementioned vascularization strategies. For example, concomitant to implantation with MSC hydrogel in the cell reservoir, NICHE drug reservoir could be loaded with pro-angiogenic factors such as Vascular Endothelial Growth Factor (VEGF) during the pre-vascularization phase, further potentiating neo-vessel formation. Alternatively, implantation of NICHE with a scaffold pre-conditioned with growth factors in the cell reservoir to tailor the architecture of the microenvironment could also be feasible [51]. We are currently exploring these strategies as we prepare to move the platform for transplantation of other cell types, namely pancreatic islets.

Direct contact of graft with blood vessels necessitates systemic immunosuppression, which is associated with a myriad of side effects spanning risk of infection, cancer development, and death [52, 53]. As an alternative to systemic immunosuppression, NICHE contains a drug reservoir that elutes immunosuppressant directly into the cell reservoir. In our study, we used CTAL4Ig as the immunosuppressant for its ability to bind to CD80 and CD86 on antigen presenting cells (APCs) and block co-stimulation through CD28 on T cells, thus inhibiting early phases of T cell activation [54, 55]. In vitro, we observed a biphasic release rate using the 8 mm$^2$ membrane surface area, which was congruent with a progressive decrease in CTLA4Ig concentration inside the drug reservoir. Notably, the release rate observed in our in vivo efficacy study mimicked in vitro behavior as plasma CTLA4Ig levels remained constant for a period of 10 days and dropped soon after, indicating a decrease in release rate. Upon transcutaneous refilling of the drug reservoir, plasma trough levels were restored, underscoring consistent drug dosing and refillability of the drug reservoir. The correlation observed between in vitro and in vivo behaviors assures straightforward dose optimization in vivo by extrapolating in vitro testing. It is noteworthy, that the plasma CTLA4Ig levels obtained with systemic administration in this study were comparable to other reports in patients and large animal studies [56-58]. However, administration of CTLA4Ig with NICHE confined drug to the transplant site and limited systemic exposure up to 12-fold while maintaining allogeneic cell survival as efficiently as with systemic dosing. Furthermore, lower accumulation of CTLA4Ig at the transplant site in locally immunosuppressed animals correlated with graft failure and higher immune cell infiltration, further emphasizing efficient localized suppression. Mechanistically, a previous report showed that high-dose CTLA4Ig treatment was able to maintain allogeneic graft survival in spite of regulatory T cell (Treg) depletion, a known side effect of CTLA4Ig treatment [59]. We speculate that grafts survived with local immunosuppression because the concentration of CTLA4Ig within the cell reservoir became high enough to suppress the host immune system at the transplant microenvironment; however, by limiting CTLA4Ig permeation into systemic circulation, Tregs were spared, resulting in a synergistic immunomodulatory effect. On the other hand, IP CTLA4Ig administration could have caused systemic immunosuppression that suppressed the host immune system even in the context of Treg depletion.

A limitation to our study is that maintenance of the allograft with local immunosuppression was only explored for a limited duration. Longer, more comprehensive studies to determine optimal dosing and immunosuppressive agents using different cell types are still warranted and will further characterize our approach. The current prevailing strategy to achieve immune evasion in the field of cell encapsulation is by physical immunoisolation using nanoporous membranes [7, 9]. However, insufficient vascularization eventually resulted in subpar graft function that led leaders in the field to move towards fully vascularized encapsulation systems that rely on undesired systemic immunosuppression [60, 61]. Our approach is novel by providing extensive vascularization of the encapsulation system and providing localized immunosuppression to circumvent the hurdles of systemic dosing. Localized immunosuppression for maintenance of transplanted allografts has been explored, although not in parallel with prevascularization. Some efforts using immunosuppressant loaded in nanoparticles targeted to the transplant site showed promise but finding a specific targeting moiety that efficiently enriches the nanoparticles to the desired site is still a major challenge [62]. Others explored in situ generation of immunosuppressant CTLA4Ig via adenoviral gene transfer in allogeneic islet [63], kidney [64], and cornea transplantation with various degrees of success. Specifically in the context of islet transplantation [63], local CTLA4Ig expression via adenoviral transduction prolonged graft survival only marginally whereas a similar approach in a kidney transplantation model prolonged graft function for up to 2 months [64]. In an approach more similar to ours, Zhang et al demonstrated that placement of a CTLA4Ig-eluting patch in the vicinity of transplanted pancreatic islets under the kidney capsule of mice prolonged graft survival over 150 days. However, even though their approach underscored promise for local immunosuppression, the patch was a separate entity to the transplanted islets and did not allow for retrievability. It is noteworthy that effective refillability and sustained dosing from NICHE drug reservoir can be exploited to further tailor the transplant microenvironment. For example, through sequential refilling of the reservoir with various immunomodulators, in single form or in cocktails, throughout the life of the transplant. This is especially important for clinical translation as clinically relevant immunosuppressive regimes go through induction and maintenance phases that employ various drugs and doses.

Conclusion

In this example we presented the development and characterization of NICHE, a dual-reservoir encapsulation system with local immunosuppressant delivery for transplantation of allogeneic cells. NICHE fabrication in nylon via SLS allowed time and cost-effective production, design optimization, and scalability. We demonstrated biocompatibility of NICHE via cytotoxicity and implantation tests in rats. By incorporating MSCs within the cell reservoir at time of implantation, we were able to drive extensive penetration of blood vessels in NICHE that were mature, functional, and connected to the systemic vasculature. Local delivery of CTLA4Ig from the drug reservoir was tunable by means of exchange area and drug concentration loaded. We successfully performed transcutaneous cell transplantation and drug reservoir refilling in subcutaneously implanted NICHE. Using an immunocompetent rat model, we demonstrated that local CTLA4Ig delivery was as effective as daily systemic dosing in maintaining viability of allogeneic cells transplanted in pre-vascularized NICHE. Moreover, local delivery confined drug to the transplant microenvironment and reduced systemic exposure up to 12-fold as compared to systemic dosing. In sum, NICHE is the first encapsulation system for transplantation of allogeneic cells that integrates extensive pre-vascularization, cell homing, and effective localized immunosuppression into a single, minimally invasive, retrievable platform, paving the way for a new cell replacement therapy approach.

Example 2. Transcutaneously Refillable Cell Confinement Platform with Local Trophic Factor Delivery The present example describes a cell confinement platform with local release of trophic factors for engraftment of functional cells. This approach is based on:

A structure of independent cell and trophic factor reservoirs constructed from biocompatible materials such as nylon, silicone, polyether ether ketone, poly-lactic acid, polycaprolactone, or any other material suitable for implantation, which can be permanent or degradable depending on the intended therapeutic deployment of the device. The shape of the device can be discoid, rectangular, cubic, cylindrical, or any other shape. The device can be fabricated by techniques such as fused deposition modeling (FDM), stereolithography (SLA), selective laser sintering (SLS), or any other method that yields the desired structure. The surface of the cell reservoir in contact with the host tissue should be at least 50% of the total device surface in contact with tissue and have fenestrations of a size that facilitates appropriate interaction between housed cells and the host. Cells housed in the cell reservoir can be pancreatic islets, Leydig cells, follicular cells, stem cells, dendritic cells, stem cell-derived β-cells, genetically engineered cells, or any other cell type that provides the desired therapeutic outcome. Furthermore, the source of cells may be autologous, allogeneic, or xenogeneic and said cells can be delivery into the reservoir exogenously (transplantation) or endogenously (recruited from the host body). The treatment of some pathologies that could benefit from this strategy could be, but are not limited to, type 1 diabetes, cancer, hypogonadism, or hypothyroidism.

A porous barrier separating the reservoirs that allows fluid communication for local diffusion of factors between reservoirs. The barrier can be of any desired porosity that insures a defined exchange/release rate for the target factor. The exchange/release rate should be tailored for each factor delivered in a way that ensures maximum permeation into the cell reservoir with minimum leaching into the systemic circulation. The porosity of the barrier could be 20 nm, 100 nm, 200 nm, 600 nm, or any other porosity. The material of the porous barrier can be steel, glass, synthetic or natural polymers, polystyrene, cellulose, glass or any other material. The porous barrier can be affixed to the mainframe of the implant by welding, gluing, fusing, or any other method that allows for filtration. Trophic factors employed in the system could be growth factors (Vascular Endothelial Growth Factor [VEGF], Fibroblast Growth Factor [FGF], angiopoietins), cytokines (lymphokines, interleukins, chemokines), immunomodulators (Cytotoxic T-Lymphocyte-Associated Protein-4—Immunoglobulin fusion protein [CTLA4Ig], Y27632, FTY720, deoxyspergualin [DSG]), or any other factor that would aid directly or indirectly in the survival or functionality of engrafted cells.

Subcutaneous implantation of the platform that allows straightforward access to loading ports, facilitating minimally invasive refillability of trophic factors or exogenously delivered cells via needle advancement through the skin. The platform can be implanted in the subcutaneous space of any region of the body suitable for best therapeutic outcome, for example the inner arm for close proximity to lymphatic-dense regions or the abdominal wall for a highly vascularized environment.

Various possible iterations of the device are depicted in FIG. 11, but any configuration that comprises independent reservoirs separated by porous materials conducive for cell engraftment could be used. An example of implementation of the disclosed approach with an implant design as in panel H of FIG. 11 for transplantation of allogeneic endocrine cells with local immunosuppression is described in Example 1 and further below.

The implant has a flat rectangular structure. The trophic factor reservoir included within the main structure of the device has a U shape and surrounds the cell reservoir on 3 sides. The top and bottom surfaces of the cell reservoir are created by 2 woven nylon meshes, an inner nylon mesh with 300 micron×300 micron openings, and an outer nylon mesh with 100 micron×100 micron openings. The meshes promote integration into the host by allowing extensive tissue and blood vessel penetration into the cell reservoir that provide a support matrix, oxygen, and nutrients to transplanted cells. As a trophic factor to promote allogeneic cell survival, immunosuppressant drug is eluted from the drug reservoir into opposing sides of the cell reservoir through two 100 nm nanoporous nylon membranes. The immunosuppressant passively diffuses to the cells and prevents their destruction by the immune system.

The exchange/release rate of trophic factors across the porous barrier may be tailored by adjusting the porosity of the barrier, the diffusion surface area, and the concentration loaded into the reservoir. In this case, release of immunosuppressant CTL4AIg and Y27632 across a 100 nm nylon membrane was adjusted by means of surface area and concentration loaded. Using small surface areas prolongs drug release across the porous membrane, while release rate follows a linear proportion to concentration loaded. Furthermore, subcutaneous implantation allows straightforward refillability of the reservoir.

Efficacy testing shows that the approach for a cell confinement platform disclosed herein is conducive for engraftment and confinement of allotransplanted endocrine cells. Furthermore, cell viability is prolonged with local administration of immunosuppressant through the implant in a comparable fashion to system intraperitoneal dosing. However, system exposure to the drug in plasma or peripheral tissues is reduced by up to 10-fold when dosed through the implant. Importantly, dosing through the implant bounds the drug to the localized tissue, with the highest concentrations inside the drug reservoir that decline in a gradient-like fashion towards the periphery. These results underscore that the disclosed approach permits the creation of a specialized environment for cell encapsulation with efficient and confined delivery of trophic factors.

Figure 12:
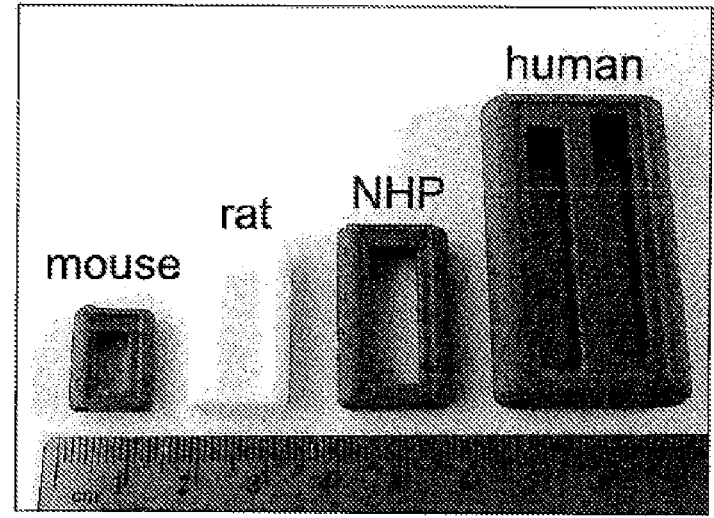
FIG. 12 depicts examples of scaled prototypes for the devices described herein. NHP =non-human primate.

The approach described herein may be scaled for use and testing across different species depending on need. FIG. 12 shows scaled implants and the below table details their dimensions.

| Species | Device dimensions (mm) | Cell reservoir dimensions (mm) | Cell reservoir volume (mm³) | Exchange surface (mm²) | Drug reservoir volume (μL) |
|---|---|---|---|---|---|
| Mice | 15 × 12 × 4.8 | 9 × 4.4 × 3.8 | 150.48 | 4 | 128 |
| Rat | 25 × 14 × 5.4 | 19 × 6 × 4.4 | 501.6 | 8 | 345 |
| NPH | 28 × 17.2 × 6.5 | 22 × 7.5 × 5.5 | 907.5 | 18 | 630 |
| Human | 50 × 29.2 × 9 | 40 × 6.1 × 6 × 2 | 3904 | 64 | 3100 |

Example 3. Implantable Therapeutic Vaccine for Sustained Long-Term Treatment and Prevention of Tumors and Cancer (Nanolymph)

The conceived therapeutic cancer vaccine nanolymph consists of an immunostimulatory implant, which allows for the local recruitment and activation of immune cells against cancer. The system includes nanoporous membranes for the sustained elution of immune adjuvants from transcutaneously refillable reservoir embedded in its structure. Through sustained diffusion, gradients of concentration of immune adjuvants are achieved across one or more cell chambers and the surrounding implant. These gradients of immune adjuvants attract and activate immune cells in the cell chambers of the nanolymph. Tumor lysate containing tumor antigens, obtained from resected tumors, metastases or biopsies are then transcutaneously injected in the cell reservoir. Once exposed to the tumor lysate, activated immune cells recognize the antigens from the tumor, activating the immune system and generating a whole-body immune surveillance and destruction of cancer and tumor cells. This can be applied to both cancerous solid and blood tumors as well as benign tumors. Unlike other vaccine approaches, nanolymph allows for a constant and sustained activation of the immune system for extended period (weeks, months, or years) without the need for boost vaccines. Further, by creating a local immune stimulatory environment, dispersion of the vaccine is prevented, providing higher efficiency and efficacy. The nanolymph can be either biodegradable or bioinert, depending on the specific clinical application.

The present example provides the nanolymph, a subcutaneously implantable vaccine platform with broad clinical applicability. The nanolymph can contain multiple reservoirs, allowing localization of vaccination components in an antigen enriched microenvironment. Acting as an artificial lymph node, the multiple reservoirs permit the use of different immune adjuvants, to independently recruit and activate immune cells (i.e., dendritic cells, B cells, and macrophages) to trigger an immunological cascade.

Figure 13:
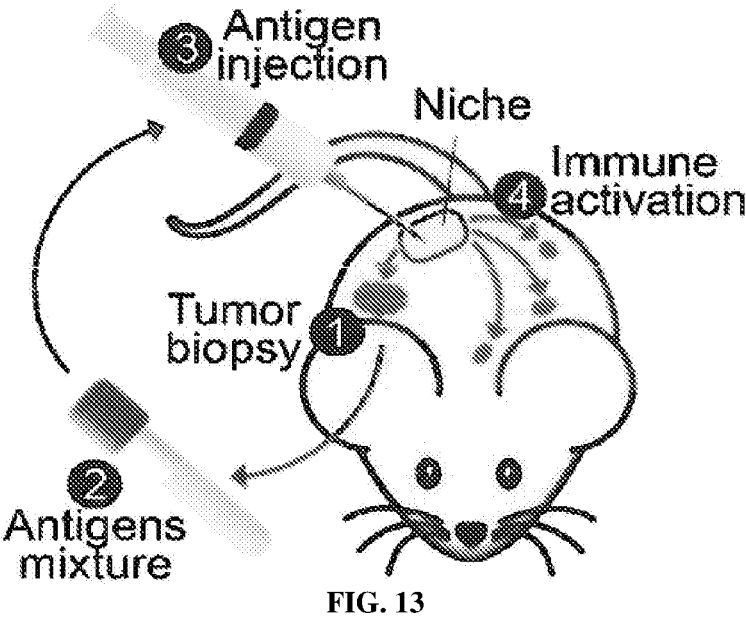
FIG. 13 depicts exemplary implementation steps for the nanolymph system described in example 3. (1) primary tumor resection; (2) preparation of antigens carrying tumor lysate; (3) transcutaneous inoculation of antigen mixture in the niche; (4) dendritic cell priming in the niche and T-cell activation against the tumor.

As an example, when applied in the setting of cancer treatment, immune adjuvants including granulocyte-macrophage colony-stimulating factor (GM-CSF), imiquimod (IMQ) and CpG ODN can be used as immunostimulants (see FIG. 13). These immune adjuvants can be used to recruit dendritic cells (DCs) to the nanolymph where they can continuously interface with tumor antigens. In this context, the nanolymph can be used for solid tumors, such as triple negative breast cancer and melanoma, as well as hematological cancers. Further, the nanolymph can be used in combination with current cancer treatment regimens, which are known strong inducers of immunogenic cell death. For example, anthracyclines, cyclophosphamide, and radiation treatment treat immunogenic cell death and in combination with the nanolymph, a synergistic effect can be achieved to boost the antitumor immunostimulatory effects.

Figure 14:
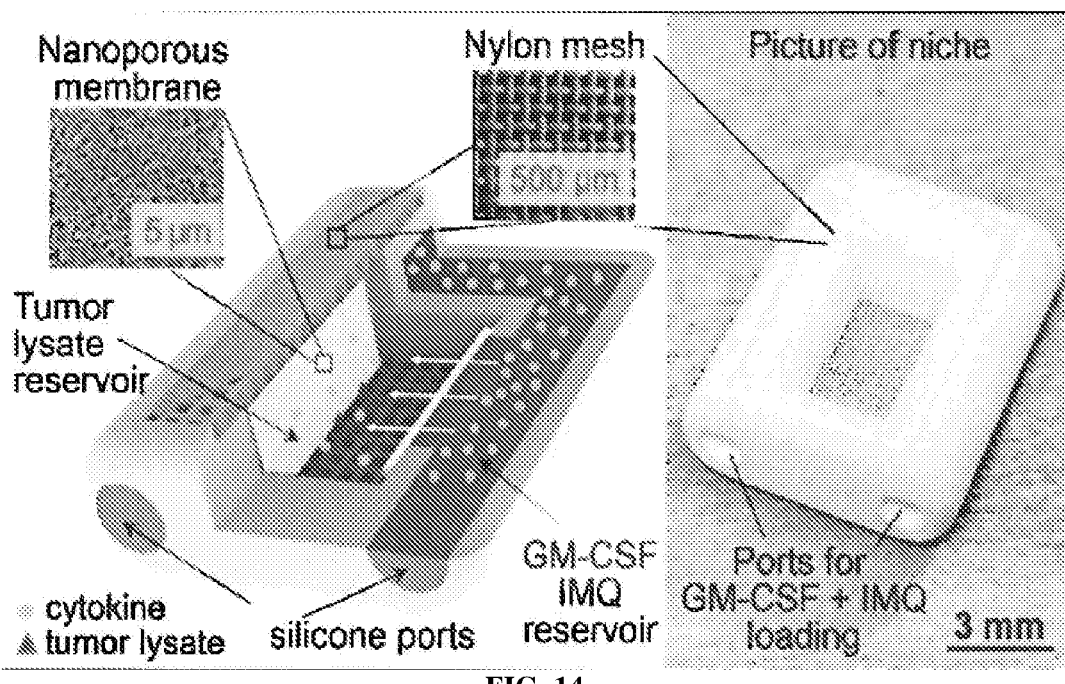
FIG. 14 depicts a representative immunostimulatory nanolymph structure as described in example 3.
Figure 15A:
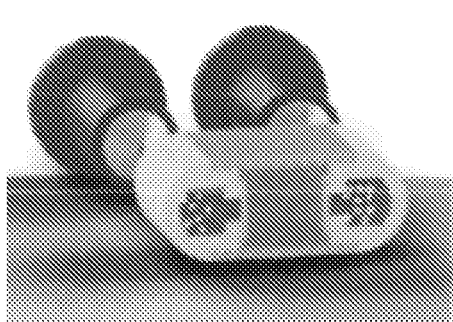
FIGS. 15A-15D depicts exemplary immune activation via the immunostimulatory nanolymph as described in example 3.
Figure 15B:
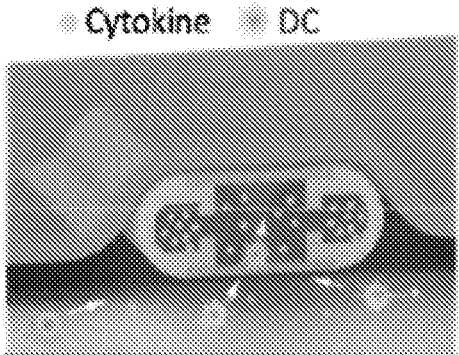
Figure 15C:
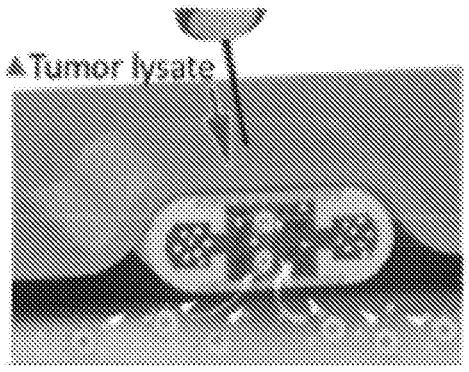
Figure 15D:
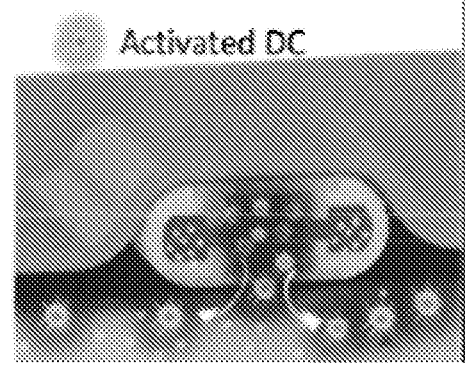

In this implementation, the nanolymph (see FIG. 14) is fabricated via 3D printing with selective laser sintering (SLS) using biocompatible polyamide PA2200. The nanolymph present five main components: 1) two biofouling-resistant nanoporous nylon membranes for controlled, sustained release of immune adjuvants from 2) drug reservoir to 3) antigen/therapeutic factors reservoir. The drug reservoir presents a "U-shape" surrounding the antigen/therapeutic factors reservoir. The niche is enclosed by 4) nylon meshes, which creates a protected microenvironment of both immune adjuvant and tumor lysate. Simultaneously, the mesh allows for DCs trafficking and transcutaneous loading of antigen/therapeutic factors. 5) Resealable implantable grade silicon ports are located on the drug reservoir permitting minimally invasive transcutaneous replenishment as needed. In this implementation, the nanolymph is deployed as depicted in FIGS. 15A=15D. Nanolymph loaded with GM-CSF and IMQ are implanted subcutaneously. Here, GM-CSF and IMQ are steadily eluted into the central reservoir creating a gradient that extends to the nanolymph surroundings to recruit DCs. With the nanolymph primed for de recruitment, autologous antigen-carrying tumor lysate is transcutaneously loaded into the central reservoir. DCs activated against tumor antigens are mobilized to secondary lymphoid organs (i.e., lymph nodes) to trigger T-cell mediated antitumor immune response.

Figure 16A:
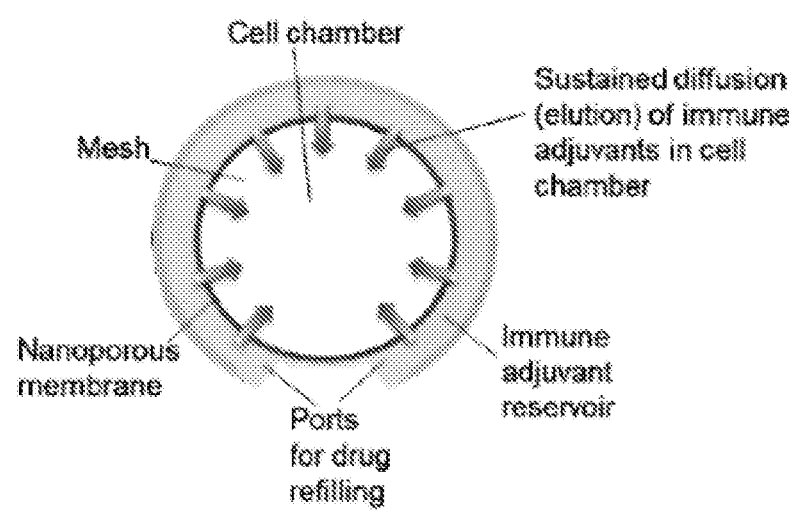
FIGS. 16A-16B depicts representative examples of nanolymph structures with circular discoidal shapes and with one (FIG. 16A) and two (FIG. 16B) drug reservoirs for the immune adjuvants.
Figure 16A:
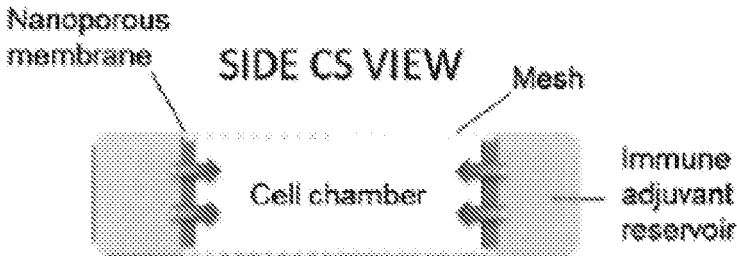
Figure 16B:
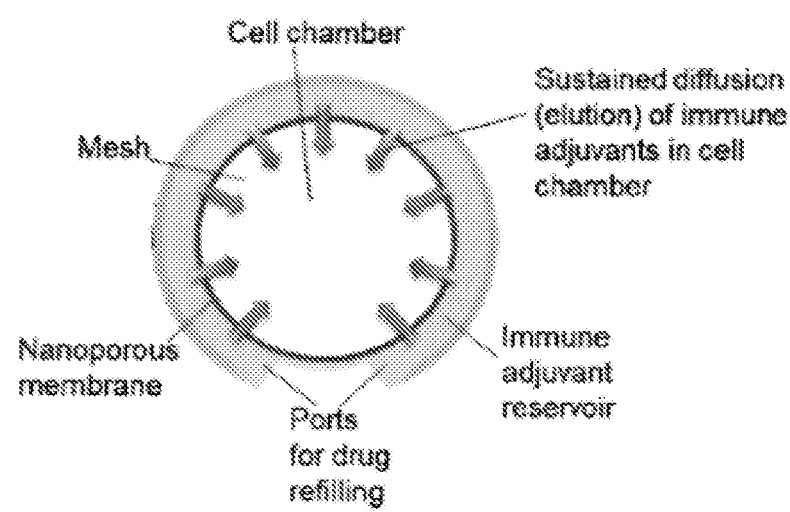
Figure 16B:
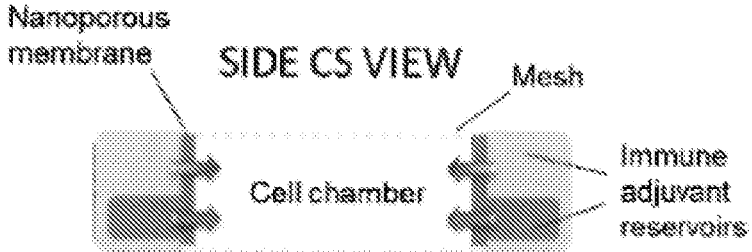

In other implementations, the nanolymph can be degradable or non-degradable. In the case of the non-degradable form, the nanolymph can be easily retrieved upon treatment termination. The nanolymph can be fabricated to be degradable over an extended period of time (i.e., 12 months). The fabrication process can be executed via 3D printing, injection molding and other polymer manufacturing techniques. The materials used can be biomedical implantable grade degradable polymers such as polylactic acid (PLA) or polycaprolactone (PCL), among others. Non-degradable materials can be nylon (polyamide and PEEK among others. The nanolymph can possess a circular discoidal (FIGS. 16A-16B), rectangular, or cylindrical shape, among others. It can contain one or more drug reservoirs and cell reservoirs. These can be used simultaneously or sequentially based on the biomedical applications.

Beyond cancer, the nanolymph has clinical applicability in various autoimmune disease. In the context of autoimmune type 1 diabetes, delivery of vaccination factors such as beta islet cell proteins or GAD65 induce a shift of islet-specific T cells to a Th2 phenotype to prevent beta cell destruction. The nanolymph can also be applied as a therapeutic vaccine platform for rheumatoid arthritis. For example, vaccine-based deliver of autoantigens, including collagen, human cartilage gp39 and dnajp1 peptide promoted sub-immunogenic presentation by dendritic cells, with the ultimate goal of inducing immunologic tolerance to subdue autoimmune manifestations. For multiple sclerosis, vaccination to induce antigen-specific tolerance with myelin proteins could be a potentiation application for the nanolymph. For therapeutic vaccination against Alzheimer's disease, amyloid beta ($A\beta$) peptides can be used as immune adjuvants, to mount an anti-AB B-cell mediated humoral response, in combination with anti-$A\beta$ targeting antibodies such as aducanumab. In addition, toll-like receptor agonists (i.e., CpG DNA) can be used as immune adjuvants to stimulate innate response.

REFERENCES

Each of the below references are hereby independently incorporated herein by reference in their entirety for all purposes.

1. Sneddon, J. B., et al., *Stem Cell Therapies for Treating Diabetes: Progress and Remaining Challenges*. Cell Stem Cell, 2018. 22 (6): p. 810-823.
2. Farina, M., et al., Cell encapsulation: *Overcoming barriers in cell transplantation in diabetes and beyond*. Adv Drug Deliv Rev, 2018.
3. Hastings, C. L., et al., *Drug and cell delivery for cardiac regeneration*. Adv Drug Deliv Rev, 2015. 84: p. 85-106.
4. Orive, G., et al., *Cell encapsulation: technical and clinical advances*. Trends Pharmacol Sci, 2015. 36 (8): p. 537-46.
5. Gamble, A., et al., *The journey of islet cell transplantation and future development*. Islets, 2018. 10 (2): p. 80-94.
6. Rickels, M. R., *Stem Cell-Derived Islets: Next Steps for Histologic and Functional Assessment During Development as a Cellular Therapy for the Treatment of Diabetes*. Diabetes, 2019. 68 (5): p. 901-903.
7. Dolgin, E., *Diabetes: Encapsulating the problem*. Nature, 2016. 540 (7632): p. S60-S62.

8. Carlsson, P. O., et al., *Transplantation of macroencapsulated human islets within the bioartificial pancreas betaAir to patients with type 1 diabetes mellitus*. Am J Transplant, 2018. 18 (7): p. 1735-1744.

9. Ludwig, B., et al., *Transplantation of human islets without immunosuppression*. Proc Natl Acad Sci USA, 2013. 110 (47): p. 19054-8.

10. Nir, T., D. A. Melton, and Y. Dor, *Recovery from diabetes in mice by beta cell regeneration*. J Clin Invest, 2007. 117 (9): p. 2553-61.

11. Hafiz, M. M., et al., *Immunosuppression and procedure-related complications in 26 patients with type 1 diabetes mellitus receiving allogeneic islet cell transplantation*. Transplantation, 2005. 80 (12): p. 1718-28.

12. Niclauss, N., et al., *Rapamycin impairs proliferation of transplanted islet beta cells*. Transplantation, 2011. 91 (7): p. 714-22.

13. Wiseman, A. C., *Immunosuppressive Medications*. Clin J Am Soc Nephrol, 2016. 11 (2): p. 332-43.

14. Anghel, D., et al., *Neurotoxicity of immunosuppressive therapies in organ transplantation*. Maedica (Buchar), 2013. 8 (2): p. 170-5.

15. Chapman, J. R., A. C. Webster, and G. Wong, *Cancer in the transplant recipient*. Cold Spring Harb Perspect Med, 2013. 3 (7).

16. Fishman, J. A., *Opportunistic infections—coming to the limits of immunosuppression?* Cold Spring Harb Perspect Med, 2013. 3 (10): p. a015669.

17. Mukherjee, S. and U. Mukherjee, *A comprehensive review of immunosuppression used for liver transplantation*. J Transplant, 2009. 2009: p. 701464.

18. Zhou, J., et al., *Spectrum of De Novo Cancers and Predictors in Liver Transplantation: Analysis of the Scientific Registry of Transplant Recipients Database*. PLOS One, 2016. 11 (5): p. e0155179.

19. Dzhonova, D. V., et al., *Local Injections of Tacrolimus-loaded Hydrogel Reduce Systemic Immunosuppression-related Toxicity in Vascularized Composite Allotransplantation*. Transplantation, 2018. 102 (10): p. 1684-1694.

20. Stepkowski, S. M., et al., *Prolongation of heterotopic heart allograft survival by local delivery of continuous low-dose cyclosporine therapy*. Transplantation, 1989. 47 (1): p. 17-23.

21. Jiang, K., et al., *Local release of dexamethasone from macroporous scaffolds accelerates islet transplant engraftment by promotion of anti-inflammatory M2 macrophages*. Biomaterials, 2017. 114: p. 71-81.

22. Weaver, J. D., et al., *Controlled Release of Dexamethasone from Organosilicone Constructs for Local Modulation of Inflammation in Islet Transplantation*. Tissue Eng Part A, 2015. 21 (15-16): p. 2250-61.

23. Pinto, E., et al., *Feasibility of localized immunosuppression: 2. PLA microspheres for the sustained local delivery of a soft immunosuppressant*. Pharmazie, 2010. 65 (6): p. 429-35.

24. Buchwald, P., et al., *Feasibility of localized immunosuppression: 1. Exploratory studies with glucocorticoids in a biohybrid device designed for cell transplantation*. Pharmazie, 2010. 65 (6): p. 421-8.

25. Song, Y., et al., *Feasibility of localized immunosuppression: 3. Preliminary evaluation of organosilicone constructs designed for sustained drug release in a cell transplant environment using dexamethasone*. Pharmazie, 2012. 67 (5): p. 394-9.

26. Gajanayake, T., et al., *A single localized dose of enzyme-responsive hydrogel improves long-term survival of a vascularized composite allograft*. Sci Transl Med, 2014. 6 (249): p. 249ra110.

27. Lu, B., et al., *Effect of a new drug releasing system on microencapsulated islet transplantation*. Int J Clin Exp Pathol, 2015. 8 (10): p. 12390-9.

28. Tao, H., et al., *Proangiogenic Features of Mesenchymal Stem Cells and Their Therapeutic Applications*. Stem Cells Int, 2016. 2016: p. 1314709.

29. Pittenger, M. F., et al., *Mesenchymal stem cell perspective: cell biology to clinical progress*. NPJ Regen Med, 2019. 4: p. 22.

30. Farina, M., et al., *Transcutaneously refillable, 3D-printed biopolymeric encapsulation system for the transplantation of endocrine cells*. Biomaterials, 2018. 177: p. 125-138.

31. Rajesh, J. J., et al., *Effect of water absorption on erosive wear behaviour of polyamides*. Journal of Materials Science, 2002. 37 (23): p. 5107-5113.

32. Teo, A. J. T., et al., *Polymeric Biomaterials for Medical Implants and Devices*. ACS Biomaterials Science & Engineering, 2016. 2 (4): p. 454-472.

33. Farah, S., et al., *Long-term implant fibrosis prevention in rodents and non-human primates using crystallized drug formulations*. Nat Mater, 2019. 18 (8): p. 892-904.

34. Pons-Faudoa, F. P., et al., *2-Hydroxypropyl-beta-cyclodextrin-enhanced pharmacokinetics of cabotegravir from a nanofluidic implant for HIV pre-exposure prophylaxis*. J Control Release, 2019. 306: p. 89-96.

35. Watt, S. M., et al., *The angiogenic properties of mesenchymal stem/stromal cells and their therapeutic potential*. Br Med Bull, 2013. 108: p. 25-53.

36. Winnacker, M., *Polyamides and their functionalization: recent concepts for their applications as biomaterials*. Biomater Sci, 2017. 5 (7): p. 1230-1235.

37. Stoia, D. I., E. Linul, and L. Marsavina, *Influence of Manufacturing Parameters on Mechanical Properties of Porous Materials by Selective Laser Sintering*. Materials (Basel), 2019. 12 (6).

38. Ligon, S. C., et al., *Polymers for 3D Printing and Customized Additive Manufacturing*. Chem Rev, 2017. 117 (15): p. 10212-10290.

39. Maitz, M. F., *Applications of synthetic polymers in clinical medicine*. Biosurface and Biotribology, 2015. 1 (3): p. 161-176.

40. Espona-Noguera, A., et al., *3D printed polyamide macroencapsulation devices combined with alginate hydrogels for insulin-producing cell-based therapies*. Int J Pharm, 2019. 566: p. 604-614.

41. Pons-Faudoa, F. P., et al., *Advanced implantable drug delivery technologies: transforming the clinical landscape of therapeutics for chronic diseases*. Biomed Microdevices, 2019. 21 (2): p. 47.

42. Lovett, M., et al., *Vascularization strategies for tissue engineering*. Tissue Eng Part B Rev, 2009. 15 (3): p. 353-70.

43. Rouwkema, J., et al., *Supply of nutrients to cells in engineered tissues*. Biotechnol Genet Eng Rev, 2010. 26: p. 163-78.

44. Farina, M., et al., *3D Printed Vascularized Device for Subcutaneous Transplantation of Human Islets*. Biotechnol J, 2017. 12 (9).

45. Li, S., et al., *A Versatile Method for Fabricating Tissue Engineering Scaffolds with a Three-Dimensional Channel for Prevasculature Networks*. ACS Appl Mater Interfaces, 2016. 8 (38): p. 25096-103.

46. Landau, S., S. Guo, and S. Levenberg, *Localization of Engineered Vasculature within 3D Tissue Constructs.* Front Bioeng Biotechnol, 2018. 6: p. 2.

47. Groot Nibbelink, M., et al., *An important step towards a prevascularized islet microencapsulation device: in vivo prevascularization by combination of mesenchymal stem cells on micropatterned membranes.* J Mater Sci Mater Med, 2018. 29 (11): p. 174.

48. Johansson, U., et al., *Formation of composite endothelial cell-mesenchymal stem cell islets: a novel approach to promote islet revascularization.* Diabetes, 2008. 57 (9): p. 2393-401.

49. Moon, J. J. and J. L. West, *Vascularization of engineered tissues: approaches to promote angio-genesis in biomaterials.* Curr Top Med Chem, 2008. 8 (4): p. 300-10.

50. Jansson, L., et al., *Pancreatic islet blood flow and its measurement.* Ups J Med Sci, 2016. 121 (2): p. 81-95.

51. Sarker, M. D., et al., *Bioprinting of Vascularized Tissue Scaffolds: Influence of Biopolymer, Cells, Growth Factors, and Gene Delivery.* J Healthc Eng, 2019. 2019: p. 9156921.

52. Diehl, R., et al., *Immunosuppression for in vivo research: state-of-the-art protocols and experimental approaches.* Cell Mol Immunol, 2017. 14 (2): p. 146-179.

53. Barlow, A. D., M. L. Nicholson, and T. P. Herbert, *Evidence for rapamycin toxicity in pancreatic beta-cells and a review of the underlying molecular mechanisms.* Diabetes, 2013. 62 (8): p. 2674-82.

54. Bluestone, J. A., E. W. St Clair, and L. A. Turka, *CTLA4Ig: bridging the basic immunology with clinical application.* Immunity, 2006. 24 (3): p. 233-8.

55. Vincenti, F., *Costimulation blockade in autoimmunity and transplantation.* J Allergy Clin Immunol, 2008. 121 (2): p. 299-306; quiz 307-8.

56. Bernett, M. J., et al., *Immune suppression in cynomolgus monkeys by XPro9523: an improved CTLA4-Ig fusion with enhanced binding to CD80, CD86 and neonatal Fc receptor FcRn.* MAbs, 2013. 5 (3): p. 384-96.

57. Chen, Y., et al., *Immunomodulatory effects induced by cytotoxic T lymphocyte antigen 4 immunoglobulin with donor peripheral blood mononuclear cell infusion in canine major histocompatibility complex-haplo-identical non-myeloablative hematopoietic cell transplantation.* Cytotherapy, 2011. 13 (10): p. 1269-80.

58. Ma, Y., et al., *Pharmacokinetics of CTLA4Ig fusion protein in healthy volunteers and patients with rheumatoid arthritis.* Acta Pharmacol Sin, 2009. 30 (3): p. 364-71.

59. Schwarz, C., et al., *The Immunosuppressive Effect of CTLA4 Immunoglobulin Is Dependent on Regulatory T Cells at Low But Not High Doses.* Am J Transplant, 2016. 16 (12): p. 3404-3415.

60. Cooper-Jones, B. and C. Ford, *Islet Cell Replacement Therapy for Insulin-Dependent Diabetes, in CADTH Issues in Emerging Health Technologies.* 2016: Ottawa (ON). p. 1-9.

61. Desai, T. and L. D. Shea, *Advances in islet encapsulation technologies.* Nat Rev Drug Discov, 2017. 16 (5): p. 338-350.

62. Patel, K., et al., *Nanotechnological Approaches to Immunosuppression and Tolerance Induction.* Curr Transplant Rep, 2017. 4 (2): p. 159-168.

63. Laumonier, T., et al., *CTLA4Ig adenoviral gene transfer induces long-term islet rat allograft survival, without tolerance, after systemic but not local intragraft expression.* Hum Gene Ther, 2003. 14 (6): p. 561-75.

64. Benigni, A., et al., *Adeno-associated virus-mediated CTLA4Ig gene transfer protects MHC-mismatched renal allografts from chronic rejection.* J Am Soc Nephrol, 2006. 17 (6): p. 1665-72.

65. Comer, R. M., et al., *Effect of administration of CTLA4-Ig as protein or cDNA on corneal allograft survival.* Invest Ophthalmol Vis Sci, 2002. 43 (4): p. 1095-103.

66. Zhang, W., et al., *Biopatterned CTLA4/Fc Matrices Facilitate Local Immunomodulation, Engraftment, and Glucose Homeostasis After Pancreatic Islet Transplantation.* Diabetes, 2016. 65 (12): p. 3660.

What is claimed is:

1. A device comprising:
a housing comprising a perimeter wall defining a cavity; and
a support structure separating the cavity into a cell chamber and a reservoir chamber, the support structure comprises a nanoporous membrane for fluid communication between the cell chamber and the reservoir chamber;
wherein the cell chamber has an outside surface that comprises at least one mesh layer; and
wherein the outside surface of the cell chamber comprises at least 50% of the total outside surface of the device.

2. The device of claim 1, wherein each mesh layer comprises a plurality of openings with an average opening size that facilitates the growth of vascular tissue into the cell chamber.

3. The device of claim 1, wherein the outside surface of the cell chamber comprises a top surface and a bottom surface, and wherein each of the top surface and the bottom surface comprises one or more mesh layers.

4. The device of claim 3, wherein each of the one or more mesh layers has a plurality of openings.

5. The device of claim 4, wherein the plurality of openings for the first mesh layer has an average opening size of about 100 microns.

6. The device of claim 1, wherein the cell chamber comprises a cell population.

7. The device of claim 6, where the cell population comprises pancreatic islet cells, Leydig cells, follicular cells, stem cells, dendritic cells, stem cell-derived b-cells, genetically engineered cells, or combinations thereof.

8. The device of claim 1, wherein the reservoir chamber contains one or more bioactive agents.

9. The device of claim 8, wherein the one or more bioactive agents comprise one or more growth factors.

10. The device of claim 8, wherein the one or more bioactive agents comprise one or more cytokines.

11. The device of claim 8, wherein the one or more bioactive agents comprise one or more immunomodulators.

12. The device of claim 1, wherein the reservoir chamber comprises one or more immune adjuvants.

13. A method of treating diabetes in a subject, comprising:
a. implanting a device according to claim 1 in the subject,
b. incubating the device until the device is infiltrated with vascular tissues; and
c. injecting insulin producing cells into the cell chamber of the devices.

14. The method of claim 13, further comprising injecting an immunosuppressant into the reservoir chamber of the device.

15. A method of treating cancer in a tumor in a subject, comprising:
a. implanting a device according to claim 1 in the subject; and b. injecting a cell lysate from a population of cells from the cancer into the cell chamber of the device.

16. The method of claim 15, further comprising injecting an immune adjuvant into the reservoir chamber of the device.

17. The device of claim 1, wherein the nanoporous membrane has a porosity ranging from about 2.5 nm to about 1000 nm.

18. A device comprising:

a housing comprising a perimeter wall defining a cavity; and a support structure separating the cavity into a cell chamber and a reservoir chamber;

wherein the cell chamber comprises a cell population and vascularized tissue;

wherein the reservoir chamber comprises one or more trophic factors;

wherein the support structure comprises a membrane configured to homogenously deliver the one or more trophic factors to the cell population in the cell chamber;

wherein the cell chamber has an outside surface that comprises at least one mesh layer; and wherein the outside surface of the cell chamber comprises at least 50% of the total outside surface of the device.

19. A device comprising:

a housing comprising a perimeter wall defining a cavity; and a support structure separating the cavity into a cell chamber and a reservoir chamber;

wherein the cell chamber comprises a cell population, one or more antigens, and vascularized tissue;

wherein the reservoir chamber comprises one or more immune adjuvants;

wherein the support structure comprises a membrane configured to homogenously deliver the one or more immune adjuvants to the cell population;

wherein the cell chamber has an outside surface that comprises at least one mesh layer; and wherein the outside surface of the cell chamber comprises at least 50% of the total outside surface of the device.

20. The device of claim 19, wherein the cell population comprises an immune cell population.

* * * * *